(12) United States Patent
Garcia et al.

(10) Patent No.: US 11,780,899 B2
(45) Date of Patent: Oct. 10, 2023

(54) ENGINEERED PROTEINS TO ENHANCE SENSITIVITY OF A CELL TO IL-2

(71) Applicants: The Board of Trustees of the Leland Stanford Junior University, Stanford, CA (US); Parker Institute for Cancer Immunotherapy, San Francisco, CA (US)

(72) Inventors: Kenan Christopher Garcia, Menlo Park, CA (US); Sean Parker, Palo Alto, CA (US); Jonathan Sockolosky, San Francisco, CA (US); Michael Hollander, Stanford, CA (US)

(73) Assignees: The Board of Trustees of the Leland Stanford Junior University, Stanford, CA (US); Parker Institute for Cancer Immunotherapy, San Francisco, CA (US)

( * ) Notice: Subject to any disclaimer, the term of this patent is extended or adjusted under 35 U.S.C. 154(b) by 208 days.

(21) Appl. No.: 16/769,535

(22) PCT Filed: Dec. 5, 2018

(86) PCT No.: PCT/US2018/064086
§ 371 (c)(1),
(2) Date: Jun. 3, 2020

(87) PCT Pub. No.: WO2019/113221
PCT Pub. Date: Jun. 13, 2019

(65) Prior Publication Data
US 2020/0385438 A1 Dec. 10, 2020

Related U.S. Application Data

(60) Provisional application No. 62/595,316, filed on Dec. 6, 2017.

(51) Int. Cl.
| | | |
|---|---|---|
| C07K 14/55 | (2006.01) | |
| C07K 14/715 | (2006.01) | |
| A61K 38/00 | (2006.01) | |

(52) U.S. Cl.
CPC .......... *C07K 14/55* (2013.01); *C07K 14/7155* (2013.01); *A61K 38/00* (2013.01); *C07K 2319/00* (2013.01)

(58) Field of Classification Search
CPC ....................................... C07K 14/55
See application file for complete search history.

(56) References Cited

U.S. PATENT DOCUMENTS

| | | |
|---|---|---|
| 9,512,194 B2 | 12/2016 | Garcia et al. |
| 2005/0158275 A1 | 7/2005 | Taylor et al. |
| 2008/0287665 A1 | 11/2008 | McCall et al. |
| 2011/0306752 A1 | 12/2011 | Wittrup et al. |
| 2013/0017168 A1 | 1/2013 | Gillies et al. |
| 2015/0218260 A1 | 8/2015 | Klein et al. |

FOREIGN PATENT DOCUMENTS

| | | |
|---|---|---|
| WO | WO2005/007121 | 1/2005 |
| WO | WO2009/103965 | 8/2009 |
| WO | WO2016/022671 | 2/2016 |

OTHER PUBLICATIONS

Rao et al.,(2005) "High-affinity CD25-binding IL-2 mutants potently stimulate persistent T cell growth", vol. 44, No. 31, pp. 10696-10701, Biochemistry.
Cosman et al., (1984) "Cloning, sequence and expression of human interleukin-2 receptor" vol. 312, pp. 768-772, Letters to Nature.
Willerford et al., (1995) "lnterleukin-2 receptor [alpha] chain regulates the size and content of the peripheral lymphoid compartment" vol. 3, No. 4 , pp. 521-530, Immunity, Cell Press.
Liu et al., (1996) "The a chain of the IL-2 receptor determines the species specificity of high-affinity IL-2 binding" vol. 8, pp. 613-621, Cytokine.
Husken et al. (1990) "Overexpression in *Escherichia coli* of a methionine free designed interleukin-2 receptor (Tac protein) based on a chemically cleavable fusion protein", European Journal of Biochemistry, vol. 192, pp. 387-394.

*Primary Examiner* — Prema M Mertz
(74) *Attorney, Agent, or Firm* — Pamela J. Sherwood; Bozicevic, Field & Francis LLP

(57) ABSTRACT

Engineered proteins, polynucleotides encoding such proteins, and methods of use thereof are provided, which engineered proteins enhance the sensitivity of a cell to IL-2.

1 Claim, 9 Drawing Sheets
Specification includes a Sequence Listing.

| Residue | Codon | Mutations | Diversity |
|---|---|---|---|
| L2 | VHM | ANDQEHILKPTV | 12 |
| D4 | GAN | DE | 2 |
| D6 | GAN | DE | 2 |
| M25 | DYR | AILMSTV | 7 |
| N27 | NNB | All | 20 |
| E29 | GAN | DE | 2 |
| L42 | NNB | All | 20 |
| I118 | MNH | RNQHILKPST | 10 |
| H120 | NNK | All | 20 |
| K153 | NNK | All | 20 |
| Theoretical Diversity | | | 1.07e9 |

| Residue | Codon | Mutations | Diversity |
|---|---|---|---|
| N27 | NNB | All | 20 |
| E29 | NVW | All but ILMFWV | 14 |
| V41 | BDS | All but ANIKMPST | 12 |
| Y42 | NNK | All | 20 |
| M43 | NNK | All | 20 |
| N59 | HVM | All but ADEGILMFWV | 10 |
| I114 | NNM | All but MW | 18 |
| H116 | NNK | All | 20 |
| Theoretical Diversity | | | 4.84e9 |

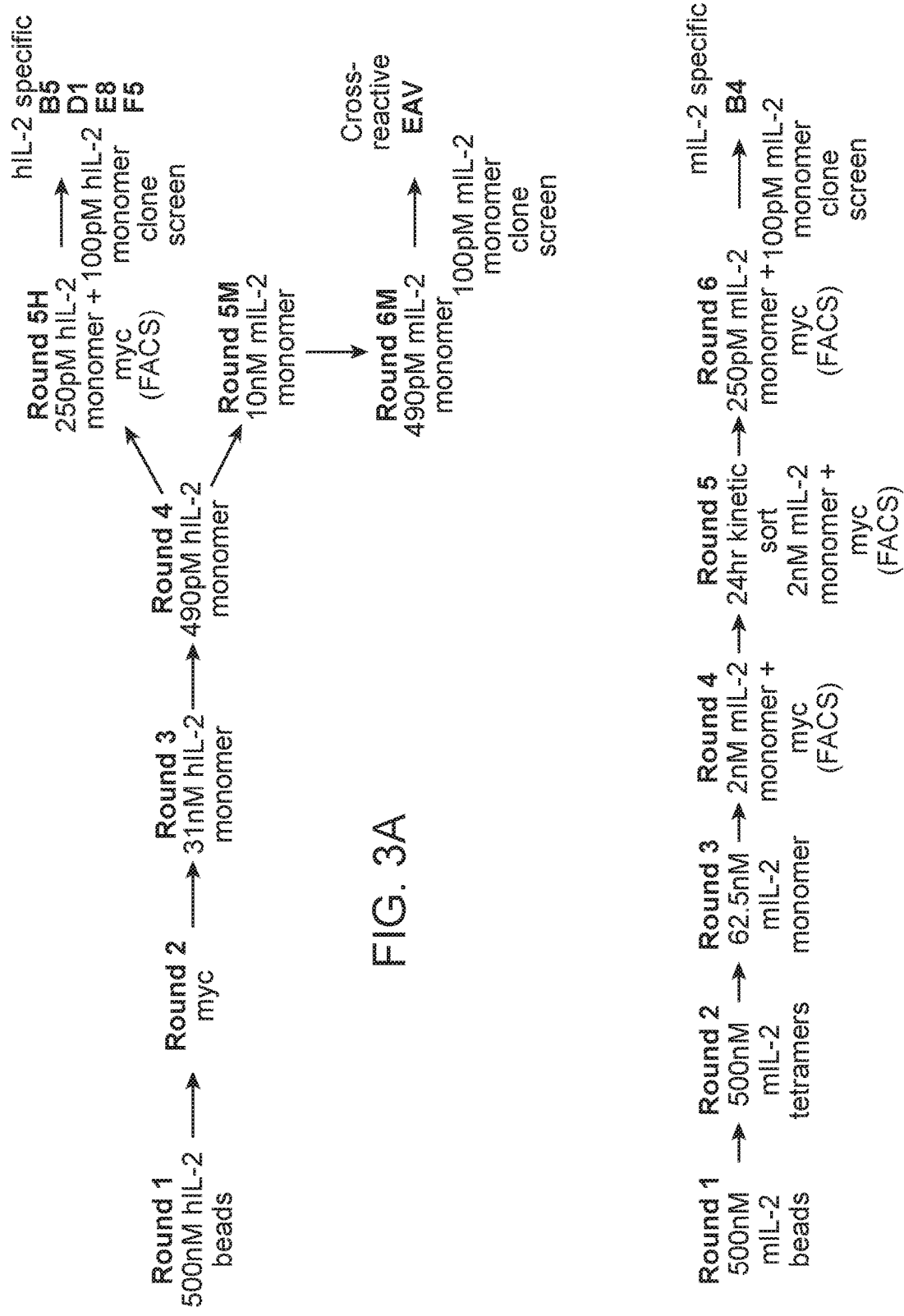

| Clone | 2 | 4 | 6 | 25 | 27 | 29 | 39 | 40 | 41 | 42 | 118 | 120 | 153 | $K_D$ for hIL-2 (nM) |
|---|---|---|---|---|---|---|---|---|---|---|---|---|---|---|
| WT | L | D | D | M | N | E | S | G | S | L | I | H | K | 2.0 |
| EAV | E | | | A | V | D | | - | T | A | T | L | E | 0.26 |
| B5 | | | | I | V | D | | | | A | R | W | Q | 0.046 |
| D1 | Q | | | I | Y | | | | | A | R | W | G | 0.027 |
| E8 | Q | | | V | Y | | | | | A | R | W | G | 0.045 |
| F5 | | | | L | V | | | | | A | N | M | G | 0.086 |

FIG. 4A

| Clone | 27 | 29 | 41 | 42 | 43 | 59 | 114 | 116 | $K_D$ for mIL-2 (nM) |
|---|---|---|---|---|---|---|---|---|---|
| WT | N | E | V | Y | M | N | I | H | 6.9 |
| B4 | E | R | W | I | V | T | E | T | 0.46 |
| EAV | | | | | | | | | 0.37 |

FIG. 4B

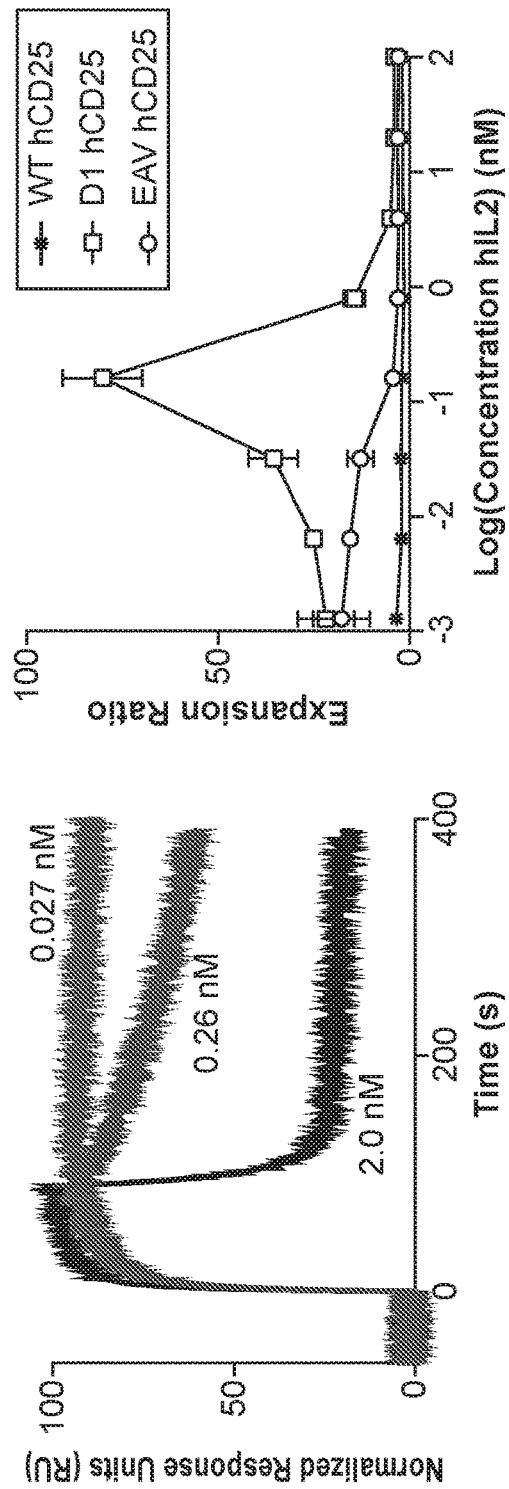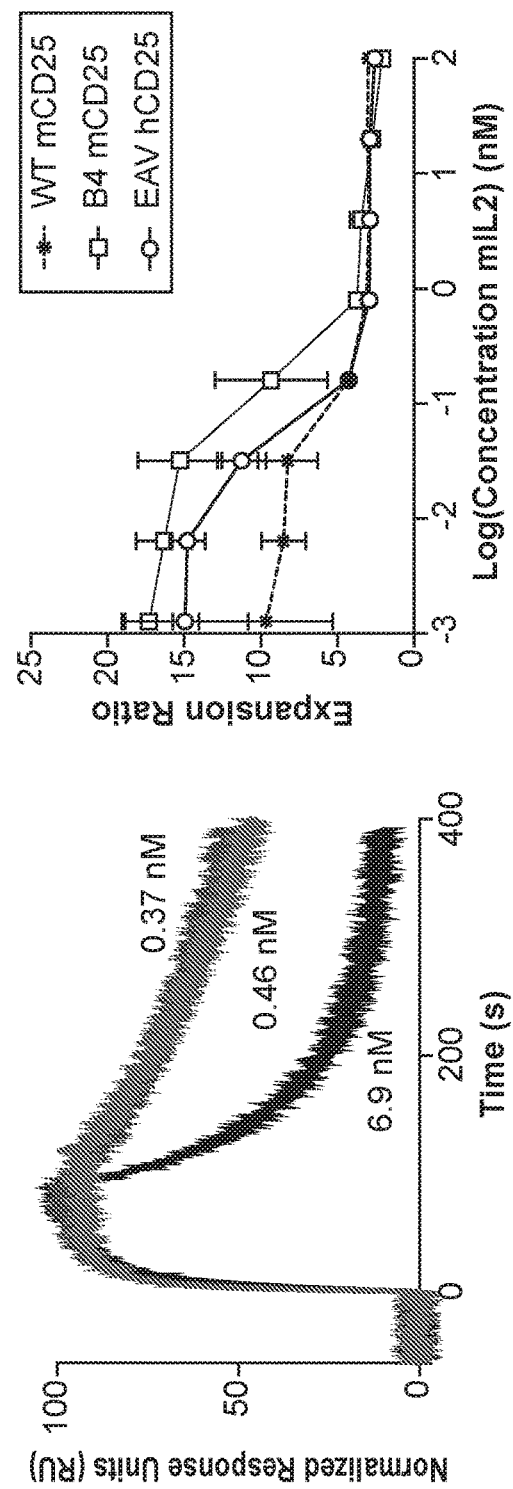
FIG. 5A
FIG. 5B

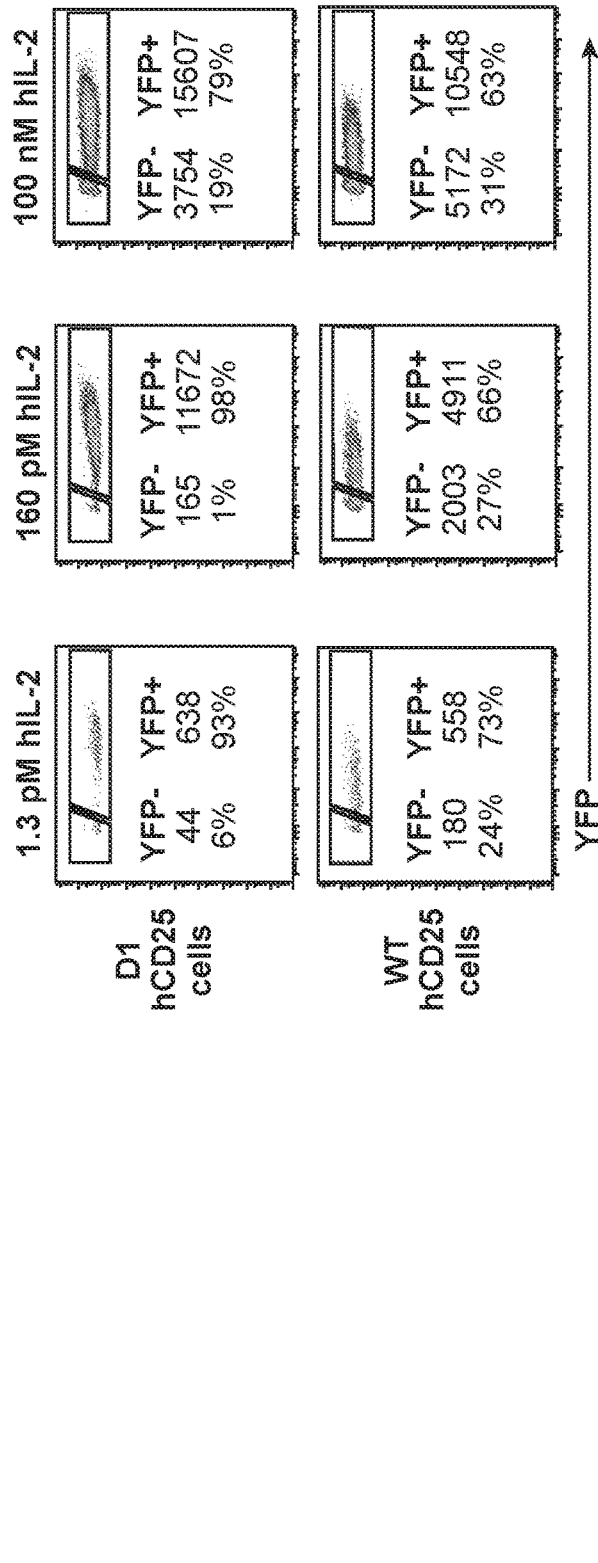
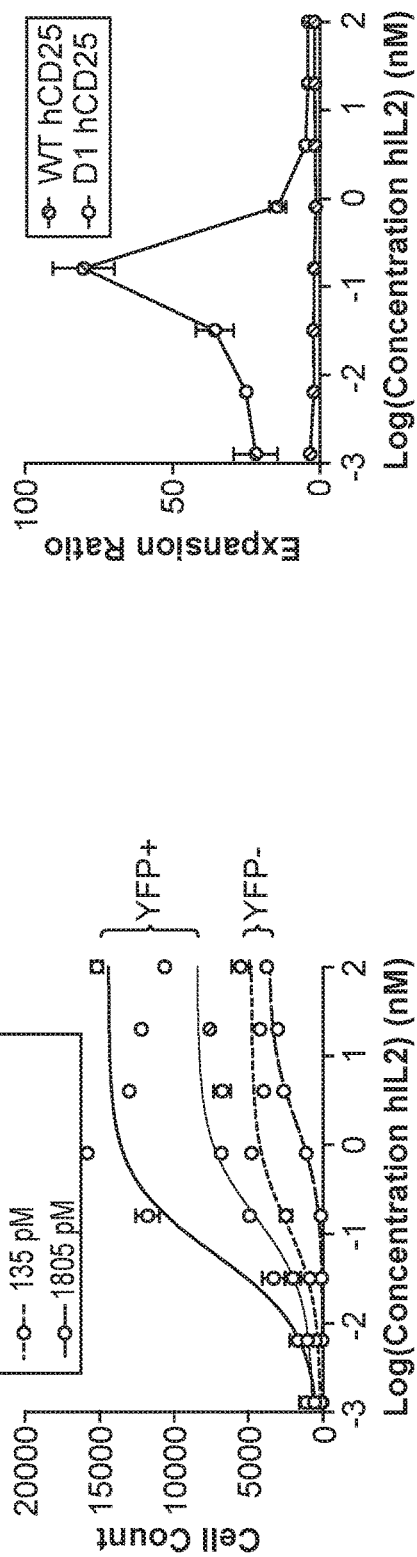
FIG. 6A
FIG. 6C
FIG. 6B

ELCDDPPEIPHATFKAMAYKEGTMLNCECKRGFRRIKSGSLYMLCTGNSSHSSWDNQCQCTSSATRNTTKQVTPQP
 2  4  6                  25 27 29          39 41                                        40 42

EEQKERKTTEMQSPMQPVDQASLPGHCREPPPWENEATERIYHFVVGQMVYYQCVQGYRALHRGPAESVCKMTHGKT
                                         118 120                                         153

RWTQPQLICTGEMETSQFPGEEKPQASPEGRPESETSCLVTTTDFQIQTEMAATMETSIFTTEYQVAVAGCVFLLIS

VLLLSGLITWQRRQRKSRRTI

FIG. 7

WT hIL-2/WT hIL-13

MLLVNQSHQGFNKEHTSKMVSAIVLYVLLAAAAHSAFAGSAPTSSSTKKTQLQLEHLLLDLQMI
LNGINNYKNPKLTRMLTFKFYMPKKATELKHLQCLEEELKPLEEVLNLAQSKNFHLRPRDLISNI
NVIVLELKGSETTFMCEYADETATIVEFLNRWITFCQSIISTLTGGGSPGPVPPSTALRELIEEL
VNITQNQKAPLCNGSMVWSINLTAGMYCAALESLINVSGCSAIEKTQRMLSGFCPHKVSAGQF
SSLHVRDTKIEVAQFVKDLLLHLRKLFREGRFNAAAHHHHHH hIL-2AK/WT hIL-13

MLLVNQSHQGFNKEHTSKMVSAIVLYVLLAAAAHSAFAGSAPTSSSTKKTQLQLEHLLLDLQMI
LNGINNYKNPKLTAMLTKKFYMPKKATELKHLQCLEEELKPLEEVLNLAQSKNFHLRPRDLISNI
NVIVLELKGSETTFMCEYADETATIVEFLNRWITFCQSIISTLTGGGSPGPVPPSTALRELIEEL
VNITQNQKAPLCNGSMVWSINLTAGMYCAALESLINVSGCSAIEKTQRMLSGFCPHKVSAGQF
SSLHVRDTKIEVAQFVKDLLLHLRKLFREGRFNAAAHHHHHH hIL-2AK/D7 hIL-13

MLLVNQSHQGFNKEHTSKMVSAIVLYVLLAAAAHSAFAGSAPTSSSTKKTQLQLEHLLLDLQMI
LNGINNYKNPKLTAMLTKKFYMPKKATELKHLQCLEEELKPLEEVLNLAQSKNFHLRPRDLISNI
NVIVLELKGSETTFMCEYADETATIVEFLNRWITFCQSIISTLTGGGSPGPVPPSTAARELIEEL
FNITQNQKAPLCNGSMVWSINLTAGMYCAALESLINVSGCSAIEKTKRMLSGFCPHKVSAGQFP
SLHVKKTRIEVAQFVKDLLIHLRKLFKEGQFNAAAHHHHHH hIL-2AKR/D7 hIL-13

MLLVNQSHQGFNKEHTSKMVSAIVLYVLLAAAAHSAFAGSAPTSSSTKKTQLQLEHLLLDLQMI
LNGINNYKNPKLTAMLTKKFYMPKKATELKHLQCLEEELKPLEEVLNLAQSKNFHLRPRDLISRI
NVIVLELKGSETTFMCEYADETATIVEFLNRWITFCQSIISTLTGGGSPGPVPPSTAARELIEEL
FNITQNQKAPLCNGSMVWSINLTAGMYCAALESLINVSGCSAIEKTKRMLSGFCPHKVSAGQFP
SLHVKKTRIEVAQFVKDLLIHLRKLFKEGQFNAAAHHHHHH

FIG. 9

ENGINEERED PROTEINS TO ENHANCE SENSITIVITY OF A CELL TO IL-2

BACKGROUND

The manipulation of cells, particularly immune cells, to differentiate, develop specialized functions and expand in numbers is of great clinical interest. Many protein factors that affect these activities are known in the art, including in particular cytokines and chemokines. However, these signaling molecules also have pleiotropic effects on cells not targeted for manipulation, and thus methods of selectively activating signaling in a targeted cell population are desirable. In particular, engineering of T cells to carry out controlled behaviors is of interest. For example, in adoptive immunotherapy T cells are isolated from blood, processed ex vivo, and re-infused into patients. T cells have been engineered for use in therapeutic applications such as the recognition and killing of cancer cells, intracellular pathogens and cells involved in autoimmunity.

A critical challenge in cell based therapies is engineering into adoptively transferred cells a desired behavior, such as activation, expansion, etc., that is protected from endogenous signaling pathways, that does not affect non-targeted endogenous cells, and that can be controlled once administered to a patient. This is particularly relevant for T cell engineering because of developmental plasticity and the immense impact that environmental factors play in determining T cell fate, function, and localization.

IL-2 is a multifunctional cytokine that plays an instrumental role in the adaptive immune response through its regulation of the homeostasis of T cells and many other immune cell lineages. IL-2 signaling controls a balance of immunostimulatory and immunosuppressive responses, rendering it an appealing, yet complicated, target for therapeutic development. The wild-type cytokine has been administered clinically for over 20 years, but at therapeutic doses it induces severe toxicity, eliciting side effects such as vascular leak syndrome. Additionally, promotion of regulatory T cell (Treg) growth blunts IL-2 efficacy in antitumor applications.

The IL-2 signaling receptor exists in two forms: the high-affinity (10 pM) heterotrimeric receptor, consisting of the IL-2Rα (CD25), IL-2Rβ (CD122), and the common cytokine receptor gamma chains (γc), and the intermediate-affinity (1 nM) heterodimeric receptor, consisting of only the IL-2Rβ and γc chains. Both the high-affinity quaternary (i.e., IL2+IL-2Rα/IL-2Rβ/γc) and intermediate-affinity ternary (i.e., IL-2+IL-2Rβ/γc) IL-2 complexes signal through interaction of the intracellular domains of IL-2Rβ and γc with JAK1 and JAK3, respectively. Whereas the IL-2Rα subunit is a private receptor for the IL-2 cytokine, IL-2Rβ is shared with the IL-15 cytokine and γc is shared with five other cytokines. IL-2Rα distinguishes the quaternary from the ternary IL-2 complex, and its expression following TCR stimulation heightens cellular sensitivity to IL-2. The IL-2Rα subunit is constitutively expressed on Tregs but not on natural killer (NK) cells or resting effector CD8$^+$ T cells, resulting in differential IL-2 potency between cell subsets. See Boynan and Sprent (2012) Nature Rev. Immunology 12:180-190.

Solution of the IL-2 quaternary complex structure offered extensive insight into the molecular properties of this cytokine system. IL-2 employs its helical faces to interact with all three receptor subunits, and there is also extensive stem contact between IL-2Rβ and γc. The interfaces between IL-2 and its three receptors are referred to in the art by binding site designations. The classical cytokine and growth factor interfaces are the IL-2/IL-2Rβ interface (site I), and IL-2/γc (site II). The IL-2/CD25 interface is referred to as Site IV. Assembly of the quaternary complex is thought to occur sequentially, with IL-2 first engaging IL-2Rα, which facilitates binding to IL-2Rβ (via the site I interface), and finally recruiting the γc subunit (via the site II interface) to lock down the high-affinity complex. See, for example, Spangler et al. (2015) Ann. Rev. Immunol. 33:139-167.

Many engineering efforts have been focused on altering the affinity of IL-2 for one or more of its receptor chains as a means to bias IL-2 activity towards cells that express either the high affinity IL-2R (CD25-positive) or intermediate affinity IL-2R (CD25-negative). IL-2 mutations at the site IV interface that showed increased affinity for CD25 potentiated growth of CD25 (IL-2Rα) positive cells compared to wild-type IL-2 (see Rao et al. (2004) Mol. Pharmacol. 66(4):864-869). The super-2 mutant of IL-2, disclosed in WO2012088446A1, which includes mutations around the hydrophobic core of IL-2 near the site I interface, has enhanced affinity for IL-2R3 and potentiates the growth of CD25-negative T cells, without altering activity on CD25-positive T cells.

Attention has also been focused on modulating the affinity of IL-2 for the IL-2Rβ and γc receptor subunits. For example, cytokine variants with mutations at the mouse IL-2 positional analogs of human IL-2 residues D20 and Q126 behave as partial agonists by obstructing IL-2Rβ and γc binding, respectively. A single IL-2 point mutant (N88R) was found to mediate selective growth of T cells over NK cells, however, Phase I clinical trials did not show any benefit of N88R compared to wild-type IL-2 treatment in HIV infection, advanced melanoma, or renal cancer, as the high doses required for therapeutic effect nullify the selective T cell growth advantage. Furthermore, recent findings indicate that vascular leak syndrome is also mediated through IL-2Rα+ endothelial cells in addition to NK cells, and thus inhibition of NK cell growth alone is not sufficient to counteract IL-2 toxicity.

Interleukin-13 (IL-13) is a cytokine secreted by T lymphocytes and mast cells, which shares several biological activities with IL-4, as a mediator of allergic inflammation and disease. An interesting feature of IL-13 biology is the nature of its receptor interactions. Its diverse functions are mediated by a complex receptor system including IL-4 receptor a (IL-4Rα; CD124) and two other cognate cell surface proteins, IL-13Rα1 (CD213α1) and IL-13Rα2 (CD213α2). IL-13Rα2 is a decoy receptor that does not appear to activate cellular signaling pathways. Interestingly, IL-13Rα2 has an extremely high affinity for IL-13, with reported affinity measurements ranging from about 100 to about 20 pM.

Compositions and methods that would allow use of IL-2 as a therapeutic with decreased toxicity are of great clinical interest, and are addressed herein.

SUMMARY

Engineered proteins, polynucleotides encoding such proteins, and methods of use thereof are provided, which engineered proteins enhance the sensitivity of a cell to IL-2. A high affinity heterotrimeric IL-2 receptor comprises IL-2Rα (CD25), IL-2Rβ (CD122), and γc chains. The CD25 protein does not directly interact with the cytoplasmic signaling apparatus associated with the receptor complex, but rather it provides high affinity binding to IL-2, and "presents" the IL-2 to the γc/CD122 components of the receptor. In one embodiment, sensitivity to IL-2 is enhanced by engineering CD25 to have increased affinity for IL-2, which therefore allows a given dose of IL-2 to have a greater effect, provided that the cells also express the γc and CD122 proteins for binding and signaling. Like CD25, IL-13Rα2 does not appear to directly interact with the cytoplasmic signaling apparatus, but binds IL-13 with extremely high affinity. When IL-2 is engineered to include IL-13 sequences sufficient for binding to IL-13Rα2, the cytokine binds to IL-13Rα2 with high affinity, which concentrates the IL-2 on the cell. IL-13Rα2 then acts as a surrogate for CD25, by presenting the engineered cytokine to the γc/CD122 components of the receptor. Cells that do not normally express IL-13Rα2, for example T cells, may be engineered to express this receptor.

In one embodiment, the engineered protein is a CD25 variant protein having increased affinity for IL-2 relative to a wild-type protein. The engineered CD25 variant proteins comprise one or more amino acid substitutions or deletions relative to the wild-type protein, and may comprise 2, 3, 4, 5, 6, 7, or more amino acid modifications, e.g., amino acid substitutions or deletions. The engineered protein may be derived, i.e., modified relative to, native human CD25. The affinity of the CD25 variant protein for IL-2 may be increased at least about 5-fold, at least about 10-fold, at least about 25-fold, at least about 50-fold, at least about 100-fold relative to the wild-type protein.

In an alternative embodiment, the engineered protein is IL-2 fused to at least a portion of IL-13 sequence, which portion is sufficient for high affinity binding to IL-13Rα2, which may be referred to herein as an IL-2/13 hybrid. The IL-2 and IL-13 sequences may be directly joined, or joined through a suitable linker. In some embodiments, the IL-13 sequence is further modified to eliminate or reduce binding to IL-13Rα1. In some embodiments, the IL-2 sequence is modified to reduce or eliminate binding to CD25, relative to the binding affinity of wild-type IL-2. The IL-2/13 hybrid protein can be administered to an individual for stimulation of IL-2 signaling. In some embodiments, the effective dose of the hybrid is lower than the effective dose of a native IL-2 protein. In some embodiments, targeted cells of interest for IL-2 sensitization are engineered to express IL-13Rα2.

In some embodiments, an engineered cell is provided, in which the cell has been modified by introduction of a variant CD25 coding sequence. Any cell can be used for this purpose. The species of the cell and the species from which the CD25 variant protein is derived may be the same or different. The engineered cell can be provided in a unit dose for therapy, and can be allogeneic, autologous, etc., with respect to an intended recipient. Introduction of the coding sequence can be performed in vivo or in vitro, using any appropriate vector, e.g., viral vectors, integrating vectors, and the like. The engineered CD25 variant may be expressed in addition to the endogenous CD25 protein; or may replace the endogenous CD25 protein, e.g., by replacement of the endogenous genomic coding sequence with the variant sequence. The engineered cell may optionally comprise a "kill switch" to delete the cell upon contacting with an appropriate signal.

In other embodiments an engineered cell is provided, which cell is modified by introduction of IL-13Rα2 coding sequences. Any cell can be used for this purpose. The species of the cell and the species from which the IL-13Rα2 is obtained may be the same or different. The engineered cell can be provided in a unit dose for therapy, and can be allogeneic, autologous, etc., with respect to an intended recipient. Introduction of the coding sequence can be performed in vivo or in vitro, using any appropriate vector, e.g., viral vectors, integrating vectors, and the like.

In some embodiments the cell is genetically modified in an ex vivo procedure, prior to transfer into a subject. In some embodiments, the genetically modified cells are expanded in vitro. An effective dose of the genetically modified cells can be administered to a patient in need thereof. In addition to the sequences encoding a variant CD25 protein or a wild-type IL-13Rα2, the cells are optionally modified to express one or both of IL-2Rβ and γc. In other embodiments the cell of interest expresses endogenous IL-2Rβ and/or γc. The engineered cell may preferentially expand in the presence of endogenous levels of IL-2, relative to an unmodified cell, and/or will preferentially expand in the presence of low levels of exogenous levels of IL-2, relative to an unmodified cell. This increased IL-2 sensitivity allows use of reduced or no exogenous IL-2, thereby reducing the toxicity associated with IL-2 therapy.

In some embodiments, the engineered cell is a T cell, including without limitation naïve CD8+ T cells, cytotoxic CD8+ T cells, naïve CD4+ T cells, helper T cells, e.g., $T_H1$, $T_H2$, $T_H9$, $T_H11$, $T_H22$, $T_{FH}$; regulatory T cells ($T_{Reg}$), e.g. $T_R1$, natural $T_{Reg}$, inducible $T_{reg}$; memory T cells, e.g., central memory T cells, stem cell memory T cells ($T_{SCM}$), effector memory T cells, NK T cells, γδ T cells; etc. In some embodiments, the engineered cells comprise a complex mixture of immune cells, e.g., tumor infiltrating lymphocytes (TILS) isolated from an individual in need of treatment. In other embodiments, the engineered cell is a stem cell, e.g. a hematopoietic stem cell, an NK cell, a macrophage, B cell, dendritic cell, etc.

In some embodiments, a vector comprising a coding sequence that encodes the CD25 variant receptor is provided, where the coding sequence is operably linked to a promoter active in the desired cell. In some embodiments, the promoter may be constitutive or inducible. In some embodiments, the promoter comprises regulatory regions of a native CD25 promoter. Various vectors are known in the art and can be used for this purpose, e.g. viral vectors, plasmid vectors, minicircle vectors, which vectors can be integrated into the target cell genome, or can be episomally maintained. The receptor encoding vector may be provided in a kit.

In some embodiments, a therapeutic method is provided, the method comprising introducing into a recipient in need thereof an engineered cell population, wherein the cell population has been modified by introduction of a sequence encoding a CD25 variant receptor of the invention; or alternatively with a sequence encoding a wild-type IL-13Rα2. The cell population may be engineered ex vivo, and is usually autologous or allogeneic with respect to the recipient. In some embodiments, IL-2 is administered to the recipient of the engineered cells, and may be administered, at reduced levels relative to conventional dosing.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

Figure 1:
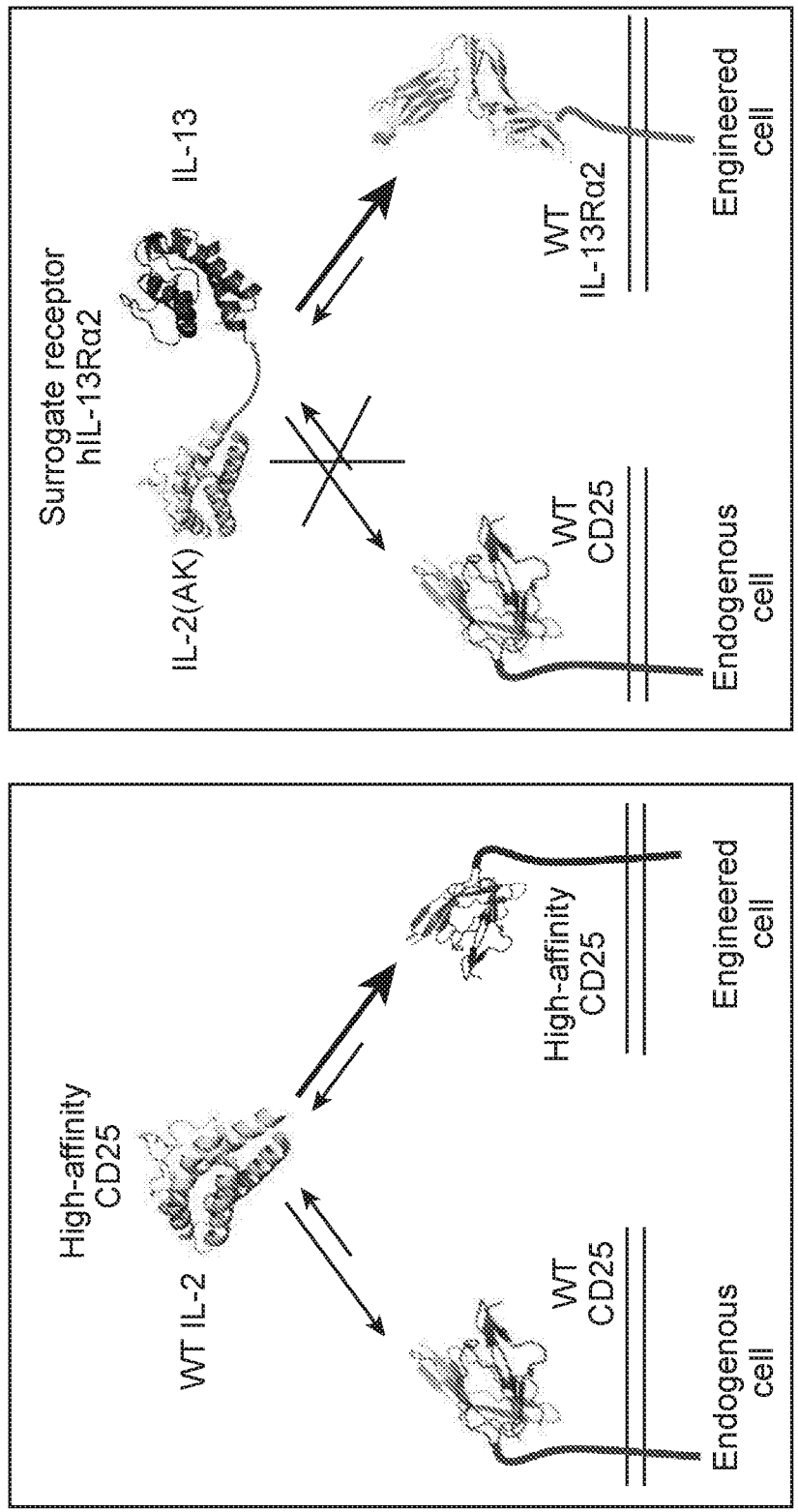
FIG. 1 is a schematic of two different approaches for sensitization to IL-2. Panel A depicts an engineered CD25 protein with increased affinity for IL-2, which can be stimulated with wild-type IL-2. Panel B depicts an engineered IL-2/13 hybrid protein with reduced affinity for CD25, which binds with high affinity to IL-13Rα2 receptor.

FIG. 2A-2B—CD25 library design. Residues at the IL-2 binding interfaces of hCD25 (FIG. 2A) and mCD25 (FIG. 2B) were randomized to create libraries of CD25 variants. The degenerate codon used for each amino acid is shown along with the allowed residues and number of possible mutations. Theoretical diversity, calculated as the product of possible residues at each position, represents the maximum number of unique CD25 variants for each library before selections. Interacting CD25 and IL-2 residues are shown in the below structures.

FIG. 3A-3B—Directed evolution of high affinity CD25. Variants of hCD25 (FIG. 3A) and mCD25 (FIG. 3B) were displayed on yeast and selected through multiple rounds of binding to biotinylated IL-2. Binding and expression were measured by streptavidin conjugated with Alexa Fluor 647 and a fluorescent myc tag antibody, respectively. Magnetic-activated cell sorting (MACS) was used during selections except as noted, when fluorescence-activated cell sorting (FACS) was used. Negative selections were run immediately before each round to clear yeast with non-specific binding to the magnetic beads and/or fluorophore used for the positive selection.

FIG. 4A-4B—Sequences and affinities of high affinity CD25 variants. DNA encoding high affinity variants was extracted after clone screens by yeast plasmid minipreps. Sequences for hCD25 (FIG. 4A) and mCD25 (FIG. 4B) clones are aligned with wild-type (WT) CD25. Residues are the same as WT except as noted, and the EAV sequence is not aligned to WT mCD25 due to differences between species. Consensus mutations for hCD25 are highlighted in blue, and deletions are marked by dashes. Affinity measurements for each clone were determined by surface plasmon resonance.

FIG. 5A-5B—High affinity CD25 variants exhibit enhanced proliferative advantages in vitro. Primary mouse T cells were activated and transduced with a retrovirus for a yellow fluorescent protein (YFP) marker and either WT or high affinity CD25. Cells were grown for 4 days at varying concentrations of mouse IL-2. Expansion was measured as the ratio of CD25-transduced (YFP+) to untransduced (YFP−) cells in each sample. Higher ratio values correspond to specific expansion of cells expressing the CD25 variant.

FIG. 6A-6C—High affinity D1 CD25 variant exhibits proliferative advantages in vitro. A mixture of transduced (YFP+) and untransduced (YFP−) cells was cultured as described in FIG. 4. After 4 days, cells were stained with a viability dye and a set volume of the cell resuspension was analyzed by FACS. Live cells were grouped into transduced and untransduced populations based on YFP intensity. The cell counts are plotted as a function of hIL-2 concentration.

FIG. 7—Sequence of WT hCD25 with mutated residues highlighted in red.

FIG. 8—Cells engineered with the surrogate hIL-13Rα2 receptor are selectively expanded with the hIL-2(AK)-hIL-13 fusion protein.

FIG. 9—Sequences of IL-2/13 hybrid proteins, SEQ ID NOs: 5, 6, 7 and 8. A signal peptide is shown in green, IL-2 in red, IL-13 in blue, and linker and tag in black.

DETAILED DESCRIPTION OF THE EMBODIMENTS

In order for the present disclosure to be more readily understood, certain terms and phrases are defined below as well as throughout the specification. The definitions provided herein are non-limiting and should be read in view of what one of skill in the art would know at the time of invention.

Definitions

Before the present methods and compositions are described, it is to be understood that this invention is not limited to the particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential methods and materials are now described. All publications mentioned herein are incorporated herein by reference to disclose and describe the methods and/or materials in connection with which the publications are cited.

As used herein and in the appended claims, the singular forms “a”, “an”, and “the” include plural referents unless the context clearly dictates otherwise. Thus, for example, reference to “a cell” includes a plurality of such cells and reference to “the peptide” includes reference to one or more peptides and equivalents thereof, e.g., polypeptides, known to those skilled in the art, and so forth.

The publications discussed herein are provided solely for their disclosure prior to the filing date of the present application. Further, the dates of publication provided may be different from the actual publication dates which may need to be independently confirmed.

Interleukin 2 (IL-2) is a pluripotent cytokine produced primarily by activated $CD4^+$ T cells and plays a crucial role in producing a normal immune response. IL-2 promotes proliferation and expansion of activated T lymphocytes, potentiates B cell growth, and activates monocytes and natural killer cells. It was by virtue of these activities that IL-2 was tested and is used as an approved treatment of cancer (aldesleukin, Proleukin®). In eukaryotic cells human IL-2 is synthesized as a precursor polypeptide of 153 amino acids, from which 20 amino acids are removed to generate mature secreted IL-2.

As used herein, “IL-2” refers to the native, or wild-type IL-2. Mature human IL-2 occurs as a 133 amino acid sequence (less the signal peptide, consisting of an additional 20 N-terminal amino acids), as described in Fujita, et. al, PNAS USA, 80, 7437-7441 (1983). The reference amino acid sequence of human IL-2 is found in Genbank under accession locator NP 000577.2. In methods where exogenous IL-2 is administered, recombinant IL-2 may be used (i.e., an IL-2 that has been prepared by recombinant DNA techniques). IL-2 is commercially available, including for pharmaceutical uses, and it is authorized for use in human patients. Suitable commercial forms include, e.g., Proleukin™, a recombinant human IL-2 composition, Aldesleukin™, an unglycosylated des-alanyl-1, serine-125 human interleukin-2 produced in E. coli, and/or Roncoleukin™, a recombinant human IL-2 produced in yeast.

For reference, the amino acid sequence of mature human IL-2 is APTSSSTKKTQLQLEHLLLDLQMILNGIN-NYKNPKLTRMLTFKFYMPKKATELKHLQCLEEELKP LEEVLNLAQSKNFHLRPRDLISNINVIVLELKG-SETTFMCEYADETATIVEFLNRWITFCQSIISTLT (SEQ ID NO:3).

As used herein, "IL-2 variant" means a polypeptide in which specific amino acid substitutions to the interleukin-2 protein, which may or may not alter its binding affinity for (CD25), IL-2Rβ (CD122), or γc, have been made. For example, IL-2 comprising both the R38A and F42K substitutions (an "AK variant") displays decreased binding to CD25. The IL-2 variants can also be characterized by amino acid insertions, deletions, substitutions and modifications at one or more sites in or at the other residues of the native IL-2 polypeptide chain. Exemplary variants can include substitutions of 1, 2, 3, 4, 5, 6, 7, 8, 9, 10 or more amino acids. Variants also include conservative modifications and substitutions at other positions of IL-2 (i.e., those that have a minimal effect on the secondary or tertiary structure of the variant). Such conservative substitutions include those described by Dayhoff in The Atlas of Protein Sequence and Structure 5 (1978), and by Argos in EMBO J., 8:779-785 (1989).

Numbering of amino acid changes will identify a chosen amino acid with reference to the position at which that amino acid normally occurs in the mature sequence of wild type human IL-2.

Interleukin-2 may be administered in combination with cells engineered to express a CD25 protein described herein. The IL-2 can be administered at a low dose relative to conventional dosing, including without limitation, wherein IL-2 is administered at a dose of about $0.05 \times 10^6$ to about $2 \times 10^6$ international unit (IU)/m$^2$/day, about $0.1 \times 10^6$ or $0.2 \times 10^6$ to about $1 \times 10^6$ IU/m$^2$/day or at a dose of less than about $3.5 \times 10^6$ IU/m$^2$/day.

Alternatively an IL-2/13 hybrid protein can be administered, where the cells may be unmodified, or may be engineered to express an IL-13Rα2 receptor. The IL-2/13 hybrid protein may be administered at a low dose relative to conventional dosing, including without limitation, wherein the hybrid is administered at a dose of about $0.05 \times 10^6$ to about $2 \times 10^6$ IU/m$^2$/day, about $0.1 \times 10^6$ or $0.2 \times 10^6$ to about $1 \times 10^6$ IU/m$^2$/day or at a dose of less than about $3.5 \times 10^6$ IU/m$^2$/day.

IL-2 supports the survival and differentiation of T lymphocytes by initiating cell signaling pathways upon interaction with the IL-2 receptor (IL-2R). IL-2 is used clinically to treat a number of human diseases including cancer and autoimmunity, and as an adjuvant to adoptive T cell therapies to promote the survival of transplanted T cells. However, IL-2 can also have apposing effects by activating off-target cell types, for example regulatory T cells. To direct the activity of IL-2 towards a specific T cell subset, the present invention provides engineered CD25 proteins with increased affinity for IL-2, allowing genetically modified cells to preferentially respond to IL-2. The administration of engineered cells allows treatment with reduced levels of exogenous IL-2, or with reliance on endogenous IL-2.

The high-affinity heterotrimeric receptor for IL-2 consists of the CD25, IL-2Rβ (CD122), and γc chains, and signals through interaction of the intracellular domains of IL-2Rβ and γc with JAK1 and JAK3, respectively. CD25 is a private receptor for IL-2. The reference sequence for human CD25 protein is publicly available at Genbank, accession number NP_000408. SEQ ID NO:1 also provides a reference for the mature sequence. Expression of IL-2Rα is tightly regulated at the transcriptional level. Several positive regulatory regions control activation-dependent IL-2Rα induction in response to antigen and IL-2.

Cells reported to express endogenous CD25 at high levels include effector T cells and $T_{Reg}$ cells which cells also express CD122 and γc receptors; cells reported to express endogenous CD25 at low levels include thymocytes, immature B cells, NK T cells, dendritic cells, Langerhans cells, endothelial cells, and fibroblasts (see Boyman and Sprent (2012) Nature Reviews Immunology 12:180-190).

Interleukin-13 (IL-13) is a cytokine secreted by T lymphocytes and mast cells, which shares several biological activities with IL-4, as a mediator of allergic inflammation and disease. IL-13 is involved in the allergic response via its actions on epithelial and smooth muscle cells. IL-13 induces many features of allergic lung disease, including airway hyperresponsiveness, goblet cell metaplasia and mucus hypersecretion, which all contribute to airway obstruction. IL-13 also induces secretion of chemokines that are required for recruitment of allergic effector cells to the lung.

For reference, the amino acid sequence of mature human IL-13 is PGPVPPSTALRELIEELVNITQNQKAPLCNG-SMVWSINLTAGMYCAALESLINVSGCSAIEKTQR MLSGFCPHKVSAGQFSSLHVRDTKI-EVAQFVKDLLLHLKKLFREGRFN (SEQ ID NO:4). Exemplary amino acid changes that alter affinity of binding to IL-13Rα1 are disclosed, for example in U.S. Pat. No. 9,512,194, specifically incorporated herein by reference. Exemplary sets of amino acid changes to IL-13 that reduce binding to IL-13Rα1 include, for example, [R11S, V18I, R86K, D87G, T88S, K89M, L101Y, K104R, K105I] or [L10V, K89R, L101N, K105E, R108T].

The human interleukin 13 receptor, alpha 2 (IL13Rα2) may be referenced with the genetic sequence of Genbank accession number NM_000640. The predicted 380-amino acid protein contains a putative signal sequence, an extracellular region with a fibronectin-like domain and typical cytokine receptor motifs, a transmembrane domain, and a short intracellular tail. IL-13Rα2 has a high affinity for IL-13, with reported affinity measurements ranging from about 100 pM to about 20 pM.

The binding properties of a binding agent, e.g. the affinity between CD25 and IL-2, IL-13 and IL-13Rα2, etc. may be measured by any method, e.g., surface plasmon resonance (SPR) or BIACORE™ analysis, Enzyme Linked Immunosorbent Assay (ELISA), x-ray crystallography, sequence analysis and scanning mutagenesis. The ability of a receptor to enhance IL-2 mediated activity, e.g., T cell proliferation, may be measured by the following methods: assays for measuring the proliferation of an IL-2 dependent cell line; assays for measuring the expression of IL-2-mediated polypeptides; assays evaluating the activity of downstream signaling molecules, e.g., JAK1 and JAK3; and other assays. A CD25 variant protein can have a statistically significant effect in one or more of these assays.

Exemplary assays for binding properties include the following: surface plasmon resonance (SPR) or Biomolecular Interaction Analysis (BIA), which detect biospecific interactions in real time, without labeling any of the interactants. Changes in the mass at the binding surface (indicative of a binding event) of the BIA chip result in alterations of the refractive index of light near the surface. The changes in the refractivity generate a detectable signal, which is measured as an indication of real-time reactions between biological molecules. Methods for using SPR are described, for example, in U.S. Pat. No. 5,641,640; H. Raether (1988) Surface Plasmons on Smooth and Rough Surfaces and on Gratings, Springer Tracts in Modern Physics (Springer Verlag); Sjolander and Urbaniczky (1991) Anal. Chem. 63:2338-2345; Szabo et al. (1995) Curr. Opin. Struct. Biol. 5:699-705 and on-line resources provided by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a molecule to a target. Such data can be used to compare different molecules. Information from SPR can also be used to develop structure-activity relationships. For example, the kinetic and equilibrium binding parameters of different molecules can be evaluated. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. "Amino acid analogs" refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acid modifications disclosed herein may include amino acid substitutions, deletions and insertions, particularly amino acid substitutions. Variant proteins may also include conservative modifications and substitutions at other positions of the cytokine and/or receptor (e.g., positions other than those involved in the affinity engineering). Such conservative substitutions include those described by Dayhoff in The Atlas of Protein Sequence and Structure 5 (1978), and by Argos in EMBO J., 8:779-785 (1989). For example, amino acids belonging to one of the following groups represent conservative changes: Group I: Ala, Pro, Gly, Gln, Asn, Ser, Thr; Group II: Cys, Ser, Tyr, Thr; Group III: Val, Ile, Leu, Met, Ala, Phe; Group IV: Lys, Arg, His; Group V: Phe, Tyr, Trp, His; and Group VI: Asp, Glu. Further, amino acid substitutions with a designated amino acid may be replaced with a conservative change.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, bi-specific antibodies, multi-specific antibodies, and fusion proteins comprising an antigen-binding portion of an antibody and a non-antibody protein. The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. Also encompassed by the term are Fab', Fv, F(ab)$_2$, and or other antibody fragments that retain specific binding to antigen, and monoclonal antibodies. As used herein, a monoclonal antibody is an antibody produced by a group of identical cells, all of which were produced from a single cell by cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778;

Huston, U.S. Pat. No. 5,476,786; and Bird, R. E. et al., Science, 242: 423-426 (1988)), regarding single chain antibodies.

The term "nanobody" (Nb), as used herein, refers to the smallest antigen binding fragment or single variable domain ($V_{HH}$) derived from a naturally occurring heavy chain antibody and is known to the person skilled in the art. They are derived from heavy chain only antibodies, seen in camelids (Hamers-Casterman et al., 1993; Desmyter et al., 1996). In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a $V_{HH}$ antibody.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); domain antibodies (dAb; Holt et al. (2003) *Trends Biotechnol.* 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH$_1$) of the heavy chain. Fab fragments differ from Fab' fragments by the addition of a few residues at the carboxyl terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. In some instances, a subject CAR may include one or more co-stimulatory domains and/or one or more co-inhibitory domains.

The term "CAR" is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled. CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application Nos. US2014/016527, US1996/017060, US2013/063083; Fedorov et al. *Sci Transl Med* (2013); 5(215):215ra172; Glienke et al. *Front Pharmacol* (2015) 6:21; Kakarla & Gottschalk 52 *Cancer J* (2014) 20(2):151-5; Riddell et al. *Cancer J* (2014) 20(2):141-4; Pegram et al. *Cancer J* (2014) 20(2):127-33; Cheadle et al. *Immunol Rev* (2014) 257(1):91-106; Barrett et al. *Annu Rev Med* (2014) 65:333-47; Sadelain et al. *Cancer Discov* (2013) 3(4):388-98; Cartellieri et al., *J Biomed Biotechnol* (2010) 956304; the disclosures of which are incorporated herein by reference in their entirety. Useful CARs also include the anti-CD194-1BB-CD3ζ CAR expressed by lentivirus loaded CTL019 (Tisagenlecleucel-T) CAR-T cells as commercialized by Novartis (Basel, Switzerland). CARs may be directed to essentially any antigen given a sufficiently specific antigen binding domain for the antigen, including e.g., cancer-specific antigens, cancer-associated antigens, antigens expressed on the surface of immune cells, pathogen antigens (e.g., viral antigens, bacterial antigens, etc.).

The term "co-stimulatory domain", as used herein, will generally refer to a stimulatory domain of a CAR that provides a secondary non-specific activation mechanism through which a primary specific stimulation is propagated. Examples of co-stimulation include antigen nonspecific T cell co-stimulation following antigen specific signaling through the T cell receptor and antigen nonspecific B cell co-stimulation following signaling through the B cell receptor. Co-stimulation, e.g., T cell co-stimulation, and the factors involved have been described in Chen & Flies. Nat Rev Immunol (2013) 13(4):227-42, the disclosure of which are incorporated herein by reference in their entirety. Co-stimulatory domains are generally polypeptides derived from receptors. In some embodiments, co-stimulatory domains homodimerize. A subject co-stimulatory domain can be an intracellular portion of a transmembrane protein (i.e., the co-stimulatory domain can be derived from a transmembrane protein). Non-limiting examples of suitable co-stimulatory polypeptides include, but are not limited to, 4-1BB (CD137), CD28, ICOS, OX-40, BTLA, CD27, CD30, GITR, and HVEM.

The term "co-inhibitory domain", as used herein, will generally refer to an inhibitory domain derived from a receptor that provides secondary inhibition of primary antigen-specific activation mechanisms which prevents co-stimulation. Co-inhibition, e.g., T cell co-inhibition, and the factors involved have been described in Chen & Flies. Nat Rev Immunol (2013) 13(4):227-42 and Thaventhiran et al. J Clin Cell Immunol (2012) S12, the disclosures of which are incorporated herein by reference in their entirety. In some embodiments, co-inhibitory domains homodimerize. A subject co-inhibitory domain can be an intracellular portion of a transmembrane protein (i.e., the co-inhibitory domain can be derived from a transmembrane protein). Non-limiting examples of suitable co-inhibitory polypeptides include, but are not limited to, CTLA-4 and PD-1.

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99%, or 100% (w/w) pure. A "separated" compound refers to a compound that is removed from at least 90% of at least one component of a sample from which the compound was obtained. Any compound described herein can be provided as an isolated or separated compound.

The terms "subject," "individual," and "patient" are used interchangeably herein to refer to a mammal being assessed for treatment and/or being treated. In some embodiments, the mammal is a human. The terms "subject," "individual," and "patient" encompass, without limitation, individuals having a disease. Subjects may be human, but also include other mammals, particularly those mammals useful as laboratory models for human disease, e.g., mice, rats, etc.

The term "sample" with reference to a patient encompasses blood and other liquid samples of biological origin, solid tissue samples such as a biopsy specimen or tissue cultures or cells derived therefrom and the progeny thereof. The term also encompasses samples that have been manipulated in any way after their procurement, such as by treatment with reagents; washed; or enrichment for certain cell populations, such as diseased cells. The definition also includes samples that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's diseased cell, e.g., a sample comprising polynucleotides and/or polypeptides that is obtained from a patient's diseased cell (e.g., a cell lysate or other cell extract comprising polynucleotides and/or polypeptides); and a sample comprising diseased cells from a patient. A biological sample comprising a diseased cell from a patient can also include non-diseased cells.

The term "diagnosis" is used herein to refer to the identification of a molecular or pathological state, disease or condition in a subject, individual, or patient.

The term "prognosis" is used herein to refer to the prediction of the likelihood of death or disease progression, including recurrence, spread, and drug resistance, in a subject, individual, or patient. The term "prediction" is used herein to refer to the act of foretelling or estimating, based on observation, experience, or scientific reasoning, the likelihood of a subject, individual, or patient experiencing a particular event or clinical outcome. In one example, a physician may attempt to predict the likelihood that a patient will survive.

As used herein, the terms "treatment," "treating," and the like, refer to administering an agent, or carrying out a procedure, for the purposes of obtaining an effect on or in a subject, individual, or patient. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of an atopic disorder or tumor in a mammal, particularly in a human, and includes: (a) inhibiting the disease, i.e., arresting its development; and (b) relieving the disease or its symptoms, i.e., causing regression of the disease or its symptoms.

Prevention of disease may include preventing the disease or a symptom of a disease from occurring in a subject which may be predisposed to the disease but has not yet been diagnosed as having it (e.g., including diseases that may be associated with or caused by a primary disease.

Treating may refer to any indicia of success in the treatment or amelioration or prevention of a disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with disease or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the engineered proteins and cells described herein. When administered in combination, each component, i.e. cell or protein, can be administered at the same time or sequentially in any order at different points in time. Thus, each component can be administered separately but sufficiently closely in time so as to provide the desired therapeutic effect.

"Concomitant administration" means administration of one or more components, such as engineered proteins and cells, known therapeutic agents, etc. at such time that the combination will have a therapeutic effect. Such concomitant administration may involve concurrent (i.e. at the same time), prior, or subsequent administration of components. A person of ordinary skill in the art would have no difficulty determining the appropriate timing, sequence and dosages of administration.

The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder. For example, a low dose of exogenous IL-2 or IL-2/13 hybrid is optionally administered in combination with a cell engineered to express a variant CD25 protein or IL-13Rα2, respectively.

A number of different cell types are suitable for engineering, e.g. to introduce a high affinity CD25 protein or IL-13Rα2 protein, for example T cells, stem cells, e.g. hematopoietic stem cells, NK cells, macrophages, B cells, dendritic cells, etc. In some embodiments the cells for engineering are autologous. In some embodiments the cells are allogeneic, for example see Brudno et al. (2016) Allogeneic T Cells That Express an Anti-CD19 Chimeric Antigen Receptor Induce Remissions of B-Cell Malignancies That Progress After Allogeneic Hematopoietic Stem-Cell Transplantation Without Causing Graft-Versus-Host Disease, Journal of Clinical Oncology 34(10)1112-1121; Hermanson et al. (2016), Induced Pluripotent Stem Cell-Derived Natural Killer Cells for Treatment of Ovarian Cancer. Stem Cells, 34: 93-101; Chabannon et al. (2016) Manufacturing Natural Killer Cells as Medicinal Products. Frontiers in Immunology. 7:504; Suck et al. (2016) NK-92: an 'off-the-shelf therapeutic' for adoptive natural killer cell-based cancer immunotherapy, Cancer Immunology, Immunotherapy 65(4):485-492, Yang et al. (2016) Phase I Study of Random Healthy Donor-Derived Allogeneic Natural Killer Cell Therapy in Patients with Malignant Lymphoma or Advanced Solid Tumors, Cancer Immunol Res; 4(3); 215-24; Redner et al. (2017) Phase 1 clinical trial of adoptive immunotherapy using "off-the-shelf" activated natural killer cells in patients with refractory and relapsed acute myeloid leukemia, Cytotherapy 19(10):1225-1232; each herein specifically incorporated by reference.

In some embodiments, the engineered cell is a T cell. The term "T cells" refers to mammalian immune effector cells that may be characterized by expression of CD3 and/or T cell antigen receptor, which cells can be engineered to express a CD25 variant or IL-13Rα2 protein. In some embodiments the T cells are selected from naïve $CD8^+$ T cells, cytotoxic $CD8^+$ T cells, naïve $CD4^+$ T cells, helper T cells, e.g. $T_H1$, $T_H2$, $T_H9$, $T_H11$, $T_H22$, $T_{FH}$; regulatory T cells, e.g. $T_R1$, natural $T_{Reg}$, inducible $T_{Reg}$; memory T cells, e.g. central memory T cells, T stem cell memory cells ($T_{SCM}$). effector memory T cells, NKT cells, γδ T cells. In some embodiments, the engineered cells comprise a complex mixture of immune cells, e.g., tumor infiltrating lymphocytes (TILs) isolated from an individual in need of treatment. See, for example, Yang and Rosenberg (2016) Adv Immunol. 130:279-94, "Adoptive T Cell Therapy for Cancer; Feldman et al (2015) Semin Oncol. 42(4):626-39 "Adoptive Cell Therapy-Tumor-Infiltrating Lymphocytes, T-Cell Receptors, and Chimeric Antigen Receptors"; Clinical Trial NCT01174121, "Immunotherapy Using Tumor Infiltrating Lymphocytes for Patients With Metastatic Cancer"; Tran et al. (2014) Science 344(6184)641-645, "Cancer immunotherapy based on mutation-specific CD4+ T cells in a patient with epithelial cancer".

In some embodiments, the T cells are contacted with endogenous IL-2 or with low levels of exogenous IL-2 or IL-2/13 hybrid proteins in vivo, i.e. where the engineered T cells are transferred to a recipient, and are contacted with an effective dose of an IL-2 protein or if engineered to express IL-13Rα2 with an effective dose of an IL-2/13 hybrid protein In other embodiments the contacting is performed in vitro.

Effector cells, for the purposes of the invention, can include autologous or allogeneic immune cells having cytolytic activity against a target cell, including without limitation tumor cells. The effector cells may have cytolytic activity that does not require recognition through the T cell antigen receptor. Cells of particular interest include cells of the T and/or NK lineage. The effector cells can be obtained by engineering peripheral blood lymphocytes (PBL) in vitro, then culturing with a cytokine and/or antigen combination that increases activation. The cells are optionally separated from non-desired cells prior to culture, prior to administration, or both. Cell-mediated cytolysis of target cells by immunological effector cells is believed to be mediated by the local directed exocytosis of cytoplasmic granules that penetrate the cell membrane of the bound target cell.

Natural killer (NK) cells are cytotoxic cells belonging to a cell class responsible for cellular cytotoxicity without prior sensitization. For example, IL-2-activated NK cells, the major effector population in lymphokine-activated killer (LAK) cells, are potent mediators of the lysis of autologous and allogeneic leukemic cells in vitro. LAK cells are non-B, non-T cells that are capable of recognizing cancer cells in a non-MHC-restricted fashion. LAK cells, which can be generated from either the normal or tumor-bearing host, appeared to represent a primitive immunosurveillance system capable of recognizing and destroying altered cells. NK cells often do not react with patient tumor cells unless they are activated by interferon, IL-2, or unless suppressor monocytes are removed from the effector cell population, and thus can benefit from engineering to express a high affinity CD25 protein. IL-2 induces proliferation of T lymphocytes and NK cells and the production of IFN-gamma; it also results in the induction of LAK cells against previously NK-resistant cell preparations and cell lines. LAK activity can be generated from human and murine T cells following engineering, and incubation with IL-2. LAK cells have been utilized in vivo both in animals and in human beings for the treatment of melanoma, renal cell carcinoma, non-Hodgkin's lymphoma, and lung and colorectal cancers.

Cytotoxic T lymphocytes (CTL) reactive to autologous tumor cells are specific effector cells for adoptive immunotherapy and are of interest for engineering according to the methods described herein. Induction and expansion of CTL is antigen-specific and MHC restricted.

Cytokine-induced killer (CIK) cells are highly efficient cytotoxic effector cells obtained by culturing peripheral blood lymphocytes (PBLs) in the presence of IFN-γ, IL-2 (or IL-12), and monoclonal antibody (MAb) against CD3, and optionally IL-1a. Cells may be cultured for at least about 1 week, at least about 2 week, at least about 3 weeks, or more, and usually not more than about 8 weeks in culture. The absolute number of CIK effector cells usually increases at least about 100-fold in such culture conditions, and may increase at least about 500-fold, at least about 1000-fold, or more. CIK cells possess a higher level of cytotoxic activity and a higher proliferation rate than LAK cells. The phenotype of the cells with the greatest cytotoxicity expresses both the T-cell marker CD3 and the NK cell marker CD56. The dominant cell phenotype in CIK cell cultures expressed the alpha-, beta-T-cell receptor (TCR-α/β). In comparison to NK cells, the cytotoxicity mediated by $CD3^+FCD56^+$ cells is also non-MHC restricted in the absence of activation, but it is non-ADCC dependent, since these double-positive cells do not express CD16. Morphologically, these cells cannot be distinguished from NK cells.

T cells collected from a subject may be separated from a mixture of cells by techniques that enrich for desired cells, or may be engineered and cultured without separation. An appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Techniques for affinity separation may include magnetic separation, using antibody-coated magnetic beads, affinity chromatography, cytotoxic agents joined to a monoclonal antibody or used in conjunction with a monoclonal antibody; e.g., complement and cytotoxins, and "panning" with antibody attached to a solid matrix, e.g., a plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g., propidium iodide). Any technique may be employed which is not unduly detrimental to the viability of the selected cells. The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum (FCS).

The collected and optionally enriched cell population may be used immediately for genetic modification, or may be frozen at liquid nitrogen temperatures and stored, being thawed and capable of being reused. The cells will usually be stored in 10% DMSO, 50% FCS, 40% RPMI 1640 medium.

The engineered cells may be infused to the subject in any physiologically acceptable medium by any convenient route of administration, normally intravascularly, although they may also be introduced by other routes, where the cells may find an appropriate site for growth. Usually, at least $1 \times 10^6$ cells/kg will be administered, at least $1 \times 10^7$ cells/kg, at least $1 \times 10^8$ cells/kg, at least $1 \times 10^9$ cells/kg, at least $1 \times 10^{10}$ cells/kg, or more, usually being limited by the number of T cells that are obtained during collection.

Expression construct: The CD25 variant or IL-13Rα2 may be introduced on an expression vector into the cell to be engineered. The CD25 variant or IL-13Rα2 may be introduced into the site of the endogenous CD25 gene, e.g., using CRISPR technology (see, for example Eyquem et al. (2017) Nature 543:113-117; Ren et al. (2017) Protein & Cell 1-10; Ren et al. (2017) Oncotarget 8(10):17002-17011). DNA encoding the receptor protein may be designed during the engineering process. An expression vector comprising the IL-2/13 hybrid protein may be introduced into a production cell line for protein synthesis and purification.

Amino acid sequence variants are prepared by introducing appropriate nucleotide changes into the coding sequence, as described herein. Such variants represent insertions, substitutions, and/or specified deletions of, residues as noted. Any combination of insertion, substitution, and/or specified deletion is made to arrive at the final construct, provided that the final construct possesses the desired biological activity as defined herein.

The nucleic acid encoding the receptor (CD25 variant or IL-13Rα2) is inserted into a vector for expression and/or integration. Many such vectors are available. For example, the CRISPR/Cas9 system can be directly applied to human cells by transfection with a plasmid that encodes Cas9 and sgRNA. The viral delivery of CRISPR components has been extensively demonstrated using lentiviral and retroviral vectors. Gene editing with CRISPR encoded by non-integrating virus, such as adenovirus and adenovirus-associated virus (AAV), has also been reported. Recent discoveries of smaller Cas proteins have enabled and enhanced the combination of this technology with vectors that have gained increasing success for their safety profile and efficiency, such as AAV vectors.

The vector components generally include, but are not limited to, one or more of the following: an origin of replication, one or more marker genes, an enhancer element, a promoter, and a transcription termination sequence. Vectors include viral vectors, plasmid vectors, integrating vectors, and the like.

The receptor (CD25 variant or IL-13Rα2) may be produced recombinantly as a fusion polypeptide with a heterologous polypeptide, e.g., a signal sequence or other polypeptide having a specific cleavage site at the N-terminus of the mature protein or polypeptide. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In mammalian cell expression the native signal sequence may be used, or other mammalian signal sequences may be suitable, such as signal sequences from secreted polypeptides of the same or related species, as well as viral secretory leaders, for example, the herpes simplex gD signal.

Expression vectors may contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors will contain a promoter that is recognized by the host organism and is operably linked to the receptor (CD25 variant or IL-13%2) coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, or from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes is often increased by inserting an enhancer sequence into the vector. Enhancers are cis-acting elements of DNA, usually about from 10 to 300 bp in length, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors for use in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

Suitable host cells for cloning or expressing the DNA in the vectors herein are the prokaryotic, yeast, or other eukaryotic cells described above. Examples of useful mammalian host cell lines are mouse L cells (L-M[TK-], ATCC #CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/–DHFR (CHO); mouse Sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells, including engineered T cells, NK cells, stem cells, etc. can be transfected with the above-described expression vectors for CD25 expression. Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Nucleic acids are "operably linked" when placed into a functional relationship with another nucleic acid sequence. For example, DNA for a signal sequence is operably linked to DNA for a polypeptide if it is expressed as a preprotein that signals the secretion of the polypeptide; a promoter or enhancer is operably linked to a coding sequence if it affects the transcription of the sequence; and a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

In the event the polypeptides or nucleic acids of the disclosure are "substantially pure," they can be at least about 60% by weight (dry weight) the biomolecule of interest. For example, the composition can be at least about 75%, about 80%, about 85%, about 90%, about 95% or about 99%, by weight, the biomolecule of interest. Purity can be measured by any appropriate standard method, for example, column chromatography, polyacrylamide gel electrophoresis, or HPLC analysis.

In another embodiment of the invention, an article of manufacture containing materials useful for the treatment of the conditions described above is provided. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). The active agent in the composition can be a vector suitable for introducing the CD25 variant into a targeted cell for expression. The label on or associated with the container indicates that the composition is used for treating the condition of choice. Further container(s) may be provided with the article of manufacture which may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

The term "sequence identity," as used herein in reference to polypeptide or DNA sequences, refers to the subunit sequence identity between two molecules. When a subunit position in both of the molecules is occupied by the same monomeric subunit (e.g., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990).

The terms "polypeptide," "protein" or "peptide" refer to any chain of amino acid residues, regardless of its length or post-translational modification (e.g., glycosylation or phosphorylation).

By "protein variant" or "variant protein" or "variant polypeptide" herein is meant a protein that differs from a wild-type protein by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent.

By "parent polypeptide", "parent protein", "precursor polypeptide", or "precursor protein" as used herein is meant an unmodified polypeptide that is subsequently modified to generate a variant. A parent polypeptide may be a wild-type (or native) polypeptide, or a variant or engineered version of a wild-type polypeptide. Parent polypeptide may refer to the polypeptide itself, compositions that comprise the parent polypeptide, or the amino acid sequence that encodes it.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

As used herein, a "therapeutically effective amount" refers to that amount of the therapeutic agent, e.g. an infusion of engineered T cells and optionally exogenous IL-2 or IL-2/13 hybrid, sufficient to treat or manage a disease or disorder. A therapeutically effective amount may refer to the amount of therapeutic agent sufficient to delay or minimize the onset of disease, e.g., to delay or minimize the spread of cancer, or the amount effective to decrease or increase signaling from a receptor of interest. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

As used herein, the terms "cancer" (or "cancerous"), or "tumor" are used to refer to cells having the capacity for autonomous growth (e.g., an abnormal state or condition characterized by rapidly proliferating cell growth). Hyperproliferative and neoplastic disease states may be categorized as pathologic (e.g., characterizing or constituting a disease state), or they may be categorized as non-pathologic (e.g., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. Pathologic hyperproliferative cells occur in disease states characterized by malignant tumor growth. Examples of non-pathologic hyperproliferative cells include proliferation of cells associated with wound repair. The terms "cancer" or "tumor" are also used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art-recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. An "adenocarcinoma" refers to a carcinoma derived from glandular tissue or in which the tumor cells form recognizable glandular structures.

Exemplary cancer types include but are not limited to AML, ALL, CML, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectal cancer, endometrial cancer, esophagus cancer, Ewing's family of tumors (e.g., Ewing's sarcoma), eye cancer, gallbladder cancer, gastrointestinal carcinoid tumors, gastrointestinal stromal tumors, gestational trophoblastic disease, Hodgkin's lymphoma, Kaposi's sarcoma, kidney cancer, laryngeal and hypopharyngeal cancer, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, or Waldenstrom's macroglobulinemia.

Compositions and Methods

Engineered CD25 variant proteins having increased affinity for IL-2 relative to a wild-type protein, polynucleotides encoding such proteins, and methods of use thereof, are provided. The engineered CD25 variant proteins comprise one or more amino acid substitutions or deletions, i.e. modifications, relative to the wild-type protein, and may comprise 2, 3, 4, 5, 6, 7, or more amino acid modifications relative to the wild-type protein, and usually not more than about 15 amino acid modifications, more usually not more than about 10 amino acid modifications. The engineered protein may be derived from, i.e. modified relative to, a native human CD25 sequence.

The affinity of the CD25 variant protein for IL-2 may be increased at least about 5-fold, at least about 10-fold, at least about 25-fold, at least about 50-fold, at least about 100-fold or more relative to the wild-type protein. For example, the $K_d$ of a high affinity CD25 variant for IL-2 may be less than about 0.5 nM, less than about 0.25 nM, less than about 0.1 nM, less than about 0.05 nM, less than about 0.04 nM, less than about 0.03 nM, less than about 0.02 nM, or less.

Amino acid modifications may be obtained by affinity maturation. An "affinity matured" polypeptide is one having one or more modification(s) in one or more residues that results in an improvement in the affinity of the CD25 protein IL-2. Affinity maturation can be done to increase the binding affinity by at least about 10% to 50%, 100%, 150% or more, or from 1 to 5 fold as compared to the "parent" polypeptide.

In some embodiments, amino acid modifications are made at one or more of the amino acids within the set of contact residues that interact with IL-2 which residues include, without limitation, L2, D4, M25, N27, E29, L42, I118, H120, K153 (for reference purposes the sequence of wild-type human CD25 is provided herein as SEQ ID NO:1, to which the numbering of amino acid modifications will refer). Additional positions for amino acid modifications may include, without limitation, S39, G40, S41. In other embodiments, modified residues are at two or more, three or more, four or more, five or more, and may comprise not more than about 10 amino acid modifications within the combined set of contact residues defined above.

In some embodiments, a human CD25 variant protein comprises one or more of the following amino acid substitutions: (1) L2Q, (2) D4E; (3) M25A, M25I, M25V, M25L; (4) N27V, N27Y; (5) E29D; (6) S39A; (7) G40A; (8) S41T; (9) L42A; (10) I118T, I118R, I118N; (10) H120L, H120W, H120M; (11) K153E, K153Q, K153G.

In some embodiments a human CD25 variant protein comprises one or more of the following amino acid substitutions: (1) L2Q; (2) M25I, M25V, M25L; (3) N27V, N27Y; (4) E29D; (5) L42A; (6) I118R, I118N; (7) H120W, H120M; (8) K153Q, K153G.

Alternatively, human CD25 variant proteins may comprise a set of amino acid modifications. Exemplary sets of such amino acid modifications include, but are not limited to: (1) {D4E; M25A, N27V, E29D, S39A, G40A, S41T, L42A, I118T, H120L, K153E}; (2) {M25I, N27V, E29D, L42A, I118R, H120W, K153Q}; (3) {L2Q, M25I, N27Y, L42A, I118R, H120W, K153G}; (4) {L2Q, M25V, N27Y, L42A, I118R, H120W}; or (5) {M25L, N27V, L42A, I118N, H120M, K153G}.

In some embodiments, the engineered CD25 variant protein is a mouse protein, where amino acid modifications are indicated relative to the native mouse CD25 protein, SEQ ID NO:2. Amino acid modifications may be made at, for example, one or more of residues N27, E29, V41, Y42, M43, N59, I114, H116. In some embodiments the amino acid modification is selected from the group consisting of N27E, E29R, V41W, Y42I, M43V, N59T, I114E and H116T, and may comprise 2, 3, 4, 5, 6, 7, 8, or more amino acid substitutions or deletions relative to the wild-type protein. In some embodiments, the variant mouse CD25 protein comprises each of the amino acid substitutions N27E, E29R, V41W, Y42I, M43V, N59T, I114E and H116T.

A high affinity variant of CD25 provides greater sensitivity to endogenous or exogenous IL-2 in a cell expressing the CD25 variant. Upon binding IL-2, the CD25 variant activates signaling that is transduced through native cellular elements or through introduced counterparts, e.g. γc and CD122 receptor components, to provide for a biological activity that mimics that native response, but which is selectively enhanced in an engineered cell expressing the CD25 variant receptor.

Also provided are engineered IL-2/13 hybrid proteins. In such embodiments an IL-2 protein is fused to at least a portion of an IL-13 protein, which portion is sufficient for high affinity binding to IL-13Rα2 (see, for example, Lupardus et al. (2010) Structure 18(3):332-342). The IL-2 sequence may be oriented so as to be amino terminal to the IL-13 sequence, or carboxy terminal.

The IL-2 and IL-13 sequences may be directly joined, or joined through a suitable linker, e.g. a peptide linker. In some embodiments, the proteins are joined by a Gly$_4$Ser linker at the fusion junction of the IL-2 and the IL-13 sequences. In some embodiments, the Gly$_4$Ser linker comprises one Gly$_4$Ser repeat. In some embodiments, the Gly$_4$Ser linker comprises two Gly$_4$Ser repeats. In some embodiments, the Gly$_4$Ser linker comprises three Gly$_4$Ser repeats. Other peptide linkers are also of interest, e.g. a flexible peptide of from about 4 to about 30 amino acids in length, e.g. from about 5 to about 20 amino acids in length, from about 5 to about 15 amino acids in length, from about 5 to about 10 amino acids in length.

The IL-2/13 hybrid may include any suitable signal peptide for expression, which signal peptide is cleaved from the mature protein. Many such signal peptides are known and used in the art, and may be selected for efficiency depending on the cell type chosen for expression of the hybrid protein.

In some embodiments, the IL-13 sequence is further modified to eliminate or reduce binding to IL-13Rα1. Exemplary amino acid changes that alter IL13 binding affinity to IL-13Rα1 are disclosed, for example in U.S. Pat. No. 9,512,194, herein specifically incorporated by reference. Exemplary sets of amino acid changes to IL-13 that reduce binding to IL-13Rα1 include, for example, {R11S, V18I, R86K, D87G, T88S, K89M, L101Y, K104R, K105T} or {L10V, K89R, L101N, K105E, R108T}, where numbering is relative to the native mature IL-13 protein.

In some embodiments, the IL-2 sequence is modified to reduce or eliminate binding to CD25. An exemplary set of amino acid changes that reduces binding to CD25 includes, for example, {R38A, F42K}, where numbering is relative to the native mature IL-2 protein.

The IL-2/13 hybrid protein can be administered to an individual in place of exogenous IL-2 to stimulate IL-2 signaling. In some embodiments, the effective dose of the hybrid is lower than the effective dose of a native IL-2 protein. Where the IL-2/13 hybrid comprises unmodified sequences relative to the wild-type proteins, a low dose is often selected. Where the IL-2/13 hybrid has been engineered to reduce binding to one or both of CD25 and IL-13Rα1, a low dose, conventional dose, or high dose of the hybrid may be administered, where a conventional dose may be from about 0.01 mg/kg/day to about 0.1 mg/kg/day.

In some embodiments, targeted cells of interest for IL-2 sensitization with an IL-2/13 hybrid are engineered to express IL-13Rα2, e.g. where the target cell is a T cell that does not naturally express the IL-13Rα2 receptor.

Methods of Treatment

Methods are provided for enhancing cellular responses using engineered cells. Such cells may be obtained, for example from the patient or an allogeneic donor, and are engineered by introduction of a receptor selected from IL-13Rα2, and CD25 variant. The engineered cells are then administered to a patient (i.e., the patient), and the introduced receptors are stimulated by contacting the engineered cell with endogenous or exogenous IL-2 or IL-2/13 hybrid, as appropriate. The methods are useful in the treatment of, for example, conditions in which enhanced T cell sensitivity to IL-2 is desired, such as enhancing killing of cancer cells with T cells; enhancing killing of pathogen-infected cells with T cells, and the like. In some instances, enhanced sensitivity to IL-2 promotes the proliferation and expansion of a desired cell population in vitro or in vivo, e.g., an immunosuppressive cell population, a cytotoxic cell population, an antigen specific cell population, or the like in response to endogenous concentrations of IL-2 or lower doses of administered IL-2.

In some embodiments, the methods may include administering to a subject in need thereof an effective amount of cells expressing a CD25 variant having increased affinity for IL-2, e.g., relative to wild-type CD25. Such cells, having increased affinity for IL-2, may be employed in essentially any context where naturally produced IL-2 or administration of IL-2, alone or in combination with other interventions (e.g., chemotherapy, immunotherapy, transplantation, antiretroviral therapy, etc.), is a bona fide treatment option and/or an investigational treatment option. Such contexts include but are not limited to e.g., cancer therapy contexts, autoimmune disease contexts, preventing transplant rejection, infection contexts, and the like.

Examples of disorders for which administration of IL-2, alone or in combination with other interventions (e.g., chemotherapy, immunotherapy, transplantation, etc.), is a bona fide treatment option and/or an investigational treatment option include but are not limited to e.g., skin cancer (e.g., melanoma, including metastatic melanoma), kidney cancer, (e.g., renal cell carcinoma (ROC), including metastatic RCC), pancreatic cancer (including pancreatic ductal adenocarcinoma), neuroblastoma, lymphoma and leukemia (e.g., non-Hodgkin's lymphoma, acute myelogenous leukemia, etc.), ovarian cancer, fallopian tube cancer, primary peritoneal cancer, breast cancer, vaginal cancer, cervical cancer, anal cancer, penile cancer, oropharyngeal cancer, non-small cell lung cancer (NSCLC), Ewing's sarcoma, rhabdomyosarcoma, systemic lupus erythematosus, rheumatoid arthritis, ankylosing spondylitis, psoriasis, Behcet's disease, Wegener's granulomatosis, Takayasu's disease, Crohn's disease, ulcerative colitis, autoimmune hepatitis, sclerosing cholangitis, Gougerot-Sjögren syndrome, alopecia areata, disorders requiring organ (e.g., liver, kidney, etc.) or tissue (e.g., bone marrow) transplantation, graft versus host disease (GVHD) and disorders treatable with stem cell transplantation (SCT) (including e.g., acute lymphoblastic leukemia, acute myelogenous leukemia, chronic myelogenous leukemia, myelodysplastic syndrome, myeloproliferative disorder, Hodgkin lymphoma, non-Hodgkin lymphoma, non-malignant diseases requiring allogeneic SCT, and the like), HIV Infection, Wiskott-Aldrich syndrome (WAS), X-linked thrombocytopenia, nephrotic syndrome, type 1 diabetes, macrophage activation syndrome, multiple sclerosis (including relapsing remitting), amyotrophic lateral sclerosis, etc.

In some instances, administration of an effective amount of cells expressing a CD25 variant having increased affinity for IL-2 allows for administration of a reduced dose of IL-2, i.e. a dose lower than would be required or indicated in the absence of the cells expressing the CD25 variant. In some instances, administration of an effective amount of cells expressing a CD25 variant having increased affinity for IL-2 may allow for no IL-2 to be administered as compared to an IL-2 treatment indicated in the absence of the cells expressing the CD25 variant. For example, in some instances, administration of an effective amount of cells expressing a CD25 variant having increased affinity for endogenous IL-2 may negate the necessity to administer IL-2.

In one embodiment, a subject having metastatic cancer (e.g., metastatic melanoma, metastatic RCC, etc.) is administered an effective amount of immune cells (e.g., T cells) expressing a CD25 variant having increased affinity for IL-2 to treat the subject for the metastatic cancer, including where the administered cells are the sole intervention to treat the subject for the metastatic cancer.

In another embodiment, a subject having metastatic cancer is co-administered an effective amount of immune cells (e.g., T cells) expressing a CD25 variant having increased affinity for IL-2 and an effective amount of IL-2 or a variant thereof, including e.g., where the effective amount of IL-2 is less than high dose IL-2, low dose IL-2 or less than low dose IL-2. Exemplary high doses of IL-2 include but are not limited to e.g., 720,000 IU/kg IV bolus every 8-16 hours for up to 15 doses and 600,000 IU per kilogram IV every 8 hours for up to 14 doses. Exemplary low doses of IL-2 include but are not limited to e.g., 2 million IU/kg subcutaneously for 14 days; 12 million IU/m2 administered subcutaneously (days 1-5 and 8-12 of each 21 day cycle); 5 million IU/m2 administered subcutaneously (days 1-5 and 8-12 of each 21 day cycle); four courses of 3 million units/m2 subcutaneously daily for 5 days followed by a 16-day rest period; and 125,000 IU/kg subcutaneously per day, for 2 weeks (2 days rest between each week).

In one embodiment, a subject having an infection (e.g., a viral infection, a bacterial infection, etc.) is administered an effective amount of immune cells (e.g., T cells, NK cells, etc.) expressing a CD25 variant having increased affinity for IL-2 to treat the subject for the infection, including where the administered cells are the sole intervention to treat the subject for the infection. In another embodiment, a subject having an infection (e.g., a viral infection, a bacterial infection, etc.) is co-administered an effective amount of immune cells (e.g., T cells, NK cells, etc.) expressing a CD25 variant having increased affinity for IL-2 and an effective amount of IL-2 or a variant thereof.

In some embodiments, in contexts where administration of exogenous IL-2, alone or in combination with other interventions (e.g., chemotherapy, immunotherapy, transplantation, antiretroviral therapy, etc.), is a bona fide treatment option and/or an investigational treatment option, administration of an IL-2/13 hybrid protein may be substituted for exogenous IL-2 administration. As described herein, cells employed in the subject methods may be engineered to express one or more desired receptors, including e.g., CD25, OD122, γc, IL-13Rα2, etc., where applicable.

The subject methods may include a step of obtaining the desired cells, e.g., T cells, NK cells, hematopoietic stem cells, etc., which may be isolated from a biological sample, or may be derived in vitro from a source of progenitor cells. The cells are transduced or transfected with a vector comprising a sequence encoding the receptor, which step may be performed in any suitable culture medium. As discussed above, the vector can integrate the variant CD25 into the genomic site of the native CD25 protein, or may provide for expression from an exogenous promoter. Generally IL-13Rα2, which is not expressed in the targeted cells, will be provided with a non-native promoter that is active in the targeted cell.

In some embodiments, an engineered cell is provided, in which the cell has been modified by introduction of a receptor selected from IL-13Rα2, and CD25 variant protein. Any cell can be used for this purpose. In some embodiments the cell is a T cell, including without limitation naïve CD8$^+$ T cells, cytotoxic CD8$^+$ T cells, naïve CD4$^+$ T cells, helper T cells, e.g. $T_H1$, $T_H2$, $T_H9$, $T_H11$, $T_H22$, $T_{FH}$; regulatory T cells, e.g. $T_R1$, natural $T_{Reg}$, inducible $T_{Reg}$; memory T cells, e.g. central memory T cells, effector memory T cells, NKT cells, γδ T cells; etc. In other embodiments, the engineered cell is a stem cell, e.g. a hematopoietic stem cell, or an NK cell. In some embodiments, the cell is genetically modified in an ex vivo procedure, prior to transfer into a subject. The engineered cell can be provided in a unit dose for therapy, and can be allogeneic, autologous, etc. with respect to an intended recipient.

In some embodiments, a vector comprising a coding sequence that encodes the IL-13Rα2 or 0025 variant is provided, where the coding sequence is operably linked to a promoter active in the desired cell; or is provided in a vector suitable for genomic insertion, e.g., by CRISPR. Various vectors are known in the art and can be used for this purpose, e.g., viral vectors, plasmid vectors, minicircle vectors, which vectors can be integrated into the target cell genome, or can be episomally maintained. The receptor encoding vector may be provided in a kit, optionally combined with an effective dose of IL-2; or with an effective dose of an IL-2/13 hybrid protein.

In some embodiments a therapeutic method is provided, the method comprising introducing into a recipient in need thereof of an engineered cell population, wherein the cell population has been modified by introduction of a sequence encoding a CD25 variant or IL-13Rα2. The cell population may be engineered ex vivo, and is usually autologous or allogeneic with respect to the recipient. In some embodiments, the introduced cell population is contacted with IL-2 or an IL-2/13 hybrid in vivo, following administration of the engineered cells, for example endogenous IL-2 or a lower than standard dose of exogenous IL-2, to reduce undesirable side effects.

A subject in need of a therapy according to the herein described methods may be a subject in need of adoptive cell transfer (ACT) to treat the subject for a condition, including e.g., cancer, infection, autoimmune disease, and the like.

In one embodiment, such a subject may be treated using ACT employing an engineered cell population that has been modified by introduction of a sequence encoding a CD25 variant or IL-13Rα2 described herein. For example, cells may be collected from a subject (e.g., a subject having a cancer or tumor, a subject having an infection, a subject having an autoimmune disease, etc.), modified ex vivo to express a CD25 variant or IL-13Rα2, and reintroduced into the subject as part of the ACT. The cells collected from the subject may be collected from any convenient and appropriate source for the ACT, including e.g., peripheral blood (e.g., the subject's peripheral blood), a biopsy (e.g., a tumor biopsy from the subject), and the like.

In some instances, the cells collected may be tumor infiltrating lymphocytes (TILs), e.g., TILs collected from a tumor of a subject. Autologous ACT using TILs allows for tumor specific immunotherapy without requiring identification of a neoantigen from a subject's tumor to be targeted. TILs modified to have increased sensitivity for IL-2, e.g., through expression of a high affinity CD25 variant, or modified to be responsive to an IL-2/13 hybrid, e.g., through expression of IL-13Rα2, allow for an increased immune response, increased tumor cell killing and/or increased maintenance/expansion of administered cells.

In some instances, the cells collected may be blood cells, e.g., NK cells collected from a subject's blood (e.g., a subject having cancer or a subject having an infection). NK cells modified to have increased sensitivity for IL-2, e.g., through expression of a high affinity CD25 variant, or modified to be responsive to an IL-2/13 hybrid, e.g., through expression of IL-13Rα2, allow for an increased immune response, increased target cell killing and/or increased maintenance/expansion of administered cells. For example, blood NK cells collected from a subject having cancer or an infection, modified to express a CD25 variant with increased affinity, and reintroduced into the subject may result in an increased immune response to the cancer or the infection. In another example, blood NK cells collected from a subject having cancer or an infection, modified to express IL-13Rα2, and reintroduced into the subject may result in increased immune activation upon administration of an IL-2/13 hybrid.

In some instances, modification of cells to be administered to a subject as part of an ACT therapy may be limited to introduction of a CD25 variant or IL-13Rα2, as described herein, and may not include introduction of other expressed therapeutic constructs. In other instances, modification of cells to be administered to a subject as part of an ACT therapy may include introduction of a CD25 variant or IL-13Rα2, as described herein, and introduction of other expressed therapeutic constructs, such as e.g., antigen-specific immunotherapeutics, including CARs, engineered T cell receptors, therapeutic antibodies and the like.

In one embodiment, a subject having a cancer or an infection may be administered an effective amount of a population of immune cells (e.g., CD8 or CD4 T cells) expressing a CAR and a CD25 variant having increased affinity for IL-2 relative to wild-type CD25. Individual immune cells of the population may express the CAR, the CD25 variant or both. The CAR may be specific for an antigen present on the surface of the cancer cells or an antigen specific to the infection such that, upon binding of the antigen the immune cell expressing the CAR is activated. Such activation of the CAR expressing immune cell may include secretion of cytokines, including IL-2. Exogenous IL-2 may or may not be administered concomitantly, including before, during or after, with the population of immune cells. Accordingly, the administered CD25 variant expressing immune cells may be stimulated upon binding of endogenous and/or lower doses of exogenous IL-2, effectively treating the subject for the cancer or the infection.

In one embodiment, a subject having a cancer or an infection may be administered an effective amount of a population of immune cells (e.g., CD4 or CD8 T cells) expressing a CAR and IL-13Rα2. Individual immune cells of the population may express both the CAR and the IL-13Rα2. The subject may be administered an IL-2/13 hybrid that binds to the IL-13Rα2 expressed by the transferred immune cells thereby activating the transferred immune cells. In some instances, IL-2/13 hybrid binding to an IL-13Rα2 expressed by the transferred immune cells may provide for selective maintenance and/or expansion of the transferred immune cells within the subject. As such cells also express a CAR specific for an antigen present on the surface of the cancer cells or an antigen specific to the infection, upon binding the cognate antigen the immune cells may be activated, thereby treating the subject for the cancer or the infection.

In one embodiment, a subject having a cancer or an infection may be administered an effective amount of a population of immune cells (e.g., CD4 or CD8 T cells) expressing an engineered TCR and a CD25 variant having increased affinity for IL-2 relative to wild-type CD25. Individual immune cells of the population may express the engineered TCR, the CD25 variant or both. The engineered TCR may be specific for an antigen expressed by the cancer cells or an antigen specific to the infection such that, upon binding of the antigen the immune cell expressing the engineered TCR is activated. Such activation of the engineered TCR expressing immune cell may include secretion of cytokines, including IL-2. Exogenous IL-2 may or may not be administered concomitantly, including before, during or after, with the population of immune cells. Accordingly, the administered CD25 variant expressing immune cells may be stimulated upon binding of endogenous and/or lower doses of exogenous IL-2, effectively treating the subject for the cancer or the infection.

In one embodiment, a subject having a cancer or an infection may be administered an effective amount of a population of immune cells (e.g., CD4 or CD8 T cells) expressing an engineered TCR and IL-13Rα2. Individual immune cells of the population may express both the engineered TCR and the IL-13Rα2. The subject may be administered an IL-2/13 hybrid that binds to the IL-13Rα2 expressed by the transferred immune cells thereby activating the transferred immune cells. In some instances, IL-2/13 hybrid binding to an IL-13Rα2 expressed by the transferred immune cells may provide for selective maintenance and/or expansion of the transferred immune cells within the subject. As such cells also express an engineered TCR specific for a cancer cell antigen or an antigen specific to the infection, upon binding the cognate antigen the immune cells may be activated, thereby treating the subject for the cancer or the infection.

Useful engineered TCRs, e.g., for treating cancer, include those having immune cell activation function in response to a cancer associated antigen. Non-limiting examples of useful TCRs include antigen-specific TCRs, Monoclonal TCRs (MTCRs), Single chain MTCRs, High Affinity CDR2 Mutant TCRs, CD1-binding MTCRs, High Affinity NY-ESO TCRs, VYG HLA-A24 Telomerase TCRs, including e.g., those described in PCT Pub Nos. WO 2003/020763, WO 2004/033685, WO 2004/044004, WO 2005/114215, WO 2006/000830, WO 2008/038002, WO 2008/039818, WO 2004/074322, WO 2005/113595, WO 2006/125962; Strommes et al. Immunol Rev. 2014; 257(1):145-64; Schmitt et al. Blood. 2013; 122(3):348-56; Chapuls et al. Sci Transl Med. 2013; 5(174):174ra27; Thaxton et al. Hum Vaccin Immunother. 2014; 10(11):3313-21 (PMID:25483644); Gschweng et al. Immunol Rev. 2014; 257(1):237-49 (PMID: 24329801); Hinrichs et al. Immunol Rev. 2014; 257(1):56-71 (PMID:24329789); Zoete et al. Front Immunol. 2013; 4:268 (PMID:24062738); Marr et al. Clin Exp Immunol. 2012; 167(2):216-25 (PMID:22235997); Zhang et al. Adv Drug Deliv Rev. 2012; 64(8):756-62 (PMID:22178904); Chhabra et al. Scientific World Journal. 2011; 11:121-9 (PMID:21218269); Boulter et al. Olin Exp Immunol. 2005; 142(3):454-60 (PMID:16297157); Sami et al. Protein Eng Des Sel. 2007; 20(8):397-403; Boulter et al. Protein Eng. 2003; 16(9):707-11; Ashfield et al. IDrugs. 2006; 9(8):554-9; Li et al. Nat Biotechnol. 2005; 23(3):349-54; Dunn et al. Protein Sci. 2006; 15(4):710-21; Liddy et al. Mal Biotechnol. 2010; 45(2); Liddy et al. Nat Med. 2012; 18(6):980-7; Oates, et al. Oncoimmunology. 2013; 2(2):e22891; McCormack, et al. Cancer Immunol Immunother. 2013 April; 62(4):773-85; Bossi et al. Cancer Immunol Immunother. 2014; 63(5):437-48 and Oates, et al. Mol Immunol. 2015 October; 67(2 Pt A):67-74; the disclosures of which are incorporated herein by reference in their entirety. In some instances, useful TCRs include those targeting one of the following antigens: NY-ESO-1, MART-1, MAGE-A3, MAGE-A3, CEA, gp100, WI1, HBV, gag (WT and/or a/6), P53, TRAIL bound to DR4, HPV-16 (E6 and/or E7), Survivin, KRAS mutants, SSX2, MAGE-A10, MAGE-A4, AFP, and the like. Engineered TCRs useful in treating infection include but are not limited to e.g., engineered TCRs directed to antigens of virial pathogens and bacterial pathogens, including e.g., those described herein.

In one embodiment, a subject having a cancer may be administered an effective amount of a population of immune cells expressing a therapeutic antibody and a CD25 variant having increased affinity for IL-2 relative to wild-type CD25. Individual immune cells of the population may express the therapeutic antibody, the CD25 variant or both. The therapeutic antibody may be specific for various antigens, including e.g., antigens present on the surface of the cancer, antigens involved in cancer-microenvironment signaling and the like. Therapeutic antibodies for the treatment of cancer may function through one or more relevant mechanisms of action, including e.g., inhibition of cancer/tumor-specific signaling (e.g., HER2 signaling, EGFR signaling, etc.), inhibition of immune evasion, delivery of a cytotoxic payload, promotion of Antibody-Dependent Cell-Mediated Cytotoxicity (ADCC), promotion of Complement Dependent Cytotoxicity (CDC), and the like. In some instances, such mechanisms may stimulate immune activation and/or cytokine release, including the stimulation of IL-2 production. Exogenous IL-2 may or may not be administered concomitantly, including before, during or after, with the population of immune cells. Accordingly, the administered CD25 variant expressing immune cells may be stimulated upon binding of endogenous and/or exogenous IL-2, effectively treating the subject for the cancer.

In one embodiment, a subject having a cancer may be administered an effective amount of a population of immune cells expressing a therapeutic antibody and IL-13Rα2. Individual immune cells of the population may express both the therapeutic antibody and the IL-13Rα2. The subject may be administered an IL-2/13 hybrid that binds to the IL-13Rα2 expressed by the transferred immune cells thereby activating the transferred immune cells. In some instances, IL-2/13 hybrid binding to an IL-13Rα2 expressed by the transferred immune cells may provide for selective maintenance and/or expansion of the transferred immune cells within the subject. As such cells also express a therapeutic antibody for the treatment of cancer, both immune cell activation and therapeutic antibody production may provide for treatment of the subject for the cancer.

Useful therapeutic antibodies for the treatment of cancer include but are not limited to e.g., Ipilimumab targeting CTLA-4 (as used in the treatment of Melanoma, Prostate Cancer, RCC); Tremelimumab targeting CTLA-4 (as used in the treatment of CRC, Gastric, Melanoma, NSCLC); Nivolumab targeting PD-1 (as used in the treatment of Melanoma, NSCLC, RCC); MK-3475 targeting PD-1 (as used in the treatment of Melanoma); Pidilizumab targeting PD-1 (as used in the treatment of Hematologic Malignancies); BMS-936559 targeting PD-L1 (as used in the treatment of Melanoma, NSCLC, Ovarian, RCC); MEDI4736 targeting PD-L1; MPDL3280A targeting PD-L1 (as used in the treatment of Melanoma); Rituximab targeting CD20 (as used in the treatment of Non-Hodgkin's lymphoma); Ibritumomab tiuxetan and tositumomab (as used in the treatment of Lymphoma); Brentuximab vedotin targeting CD30 (as used in the treatment of Hodgkin's lymphoma); Gemtuzumab ozogamicin targeting CD33 (as used in the treatment of Acute myelogenous leukaemia); Alemtuzumab targeting CD52 (as used in the treatment of Chronic lymphocytic leukaemia); IGN101 and adecatumumab targeting EpCAM (as used in the treatment of Epithelial tumors (breast, colon and lung)); Labetuzumab targeting CEA (as used in the treatment of Breast, colon and lung tumors); huA33 targeting gpA33 (as used in the treatment of Colorectal carcinoma); Pemtumomab and oregovomab targeting Mucins (as used in the treatment of Breast, colon, lung and ovarian tumors); CC49 (minretumomab) targeting TAG-72 (as used in the treatment of Breast, colon and lung tumors); cG250 targeting CAIX (as used in the treatment of Renal cell carcinoma); J591 targeting PSMA (as used in the treatment of Prostate carcinoma); MOv18 and MORAb-003 (farletuzumab) targeting Folate-binding protein (as used in the treatment of Ovarian tumors); 3F8, ch14.18 and KW-2871 targeting Gangliosides (such as GD2, GD3 and GM2) (as used in the treatment of Neuroectodermal tumors and some epithelial tumors); hu3S193 and IgN311 targeting Le y (as used in the treatment of Breast, colon, lung and prostate tumors); Bevacizumab targeting VEGF (as used in the treatment of Tumor vasculature); IM-2C6 and CDP791 targeting VEGFR (as used in the treatment of Epithelium-derived solid tumors); Etaracizumab targeting Integrin_V_3 (as used in the treatment of Tumor vasculature); Volociximab targeting Integrin_5_1 (as used in the treatment of Tumor vasculature); Cetuximab, panitumumab, nimotuzumab and 806 targeting EGFR (as used in the treatment of Glioma, lung, breast, colon, and head and neck tumors); Trastuzumab and pertuzumab targeting ERBB2 (as used in the treatment of Breast, colon, lung, ovarian and prostate tumors); MM-121 targeting ERBB3 (as used in the treatment of Breast, colon, lung, ovarian and prostate, tumors); AMG 102, METMAB and SCH 900105 targeting MET (as used in the treatment of Breast, ovary and lung tumors); AVE1642, IMC-A12, MK-0646, R1507 and CP 751871 targeting IGF1R (as used in the treatment of Glioma, lung, breast, head and neck, prostate and thyroid cancer); KB004 and IIIA4 targeting EPHA3 (as used in the treatment of Lung, kidney and colon tumors, melanoma, glioma and haematological malignancies); Mapatumumab (HGS-ETR1) targeting TRAILR1 (as used in the treatment of Colon, lung and pancreas tumors and haematological malignancies); HGS-ETR2 and CS-1008 targeting TRAILR2; Denosumab targeting RANKL (as used in the treatment of Prostate cancer and bone metastases); Sibrotuzumab and F19 targeting FAP (as used in the treatment of Colon, breast, lung, pancreas, and head and neck tumors); 8106 targeting Tenascin (as used in the treatment of Glioma, breast and prostate tumors); Blinatumomab (Blincyto; Amgen) targeting CD3 (as used in the treatment of ALL); pembrolizumab targeting PD-1 as used in cancer immunotherapy; 9E10 antibody targeting c-Myc; and the like.

Similar approaches may also be utilized for the treatment of infectious diseases. For example, in one embodiment, a subject having an infection (e.g., a viral infection, a bacterial infection) may be administered an effective amount of a population of immune cells expressing a therapeutic antibody and a CD25 variant having increased affinity for IL-2 relative to wild-type CD25. Individual immune cells of the population may express the therapeutic antibody, the CD25 variant or both. The therapeutic antibody may be specific for various pathogen antigens, including e.g., viral antigens, bacterial antigens, and the like.

In one embodiment, a subject having an infection may be administered an effective amount of a population of immune cells expressing a therapeutic antibody and IL-13Rα2. Individual immune cells of the population may express both the therapeutic antibody and the IL-13Rα2. The subject may be administered an IL-2/13 hybrid that binds to the IL-13Rα2 expressed by the transferred immune cells thereby activating the transferred immune cells. In some instances, IL-2/13 hybrid binding to an IL-13Rα2 expressed by the transferred immune cells may provide for selective maintenance and/or expansion of the transferred immune cells within the subject. As such cells also express a therapeutic antibody for the treatment of the infection, both immune cell activation and therapeutic antibody production may provide for treatment of the subject for the infection.

In some embodiments, ACT using cells having increased sensitivity for IL-2, e.g., through expression of a high affinity CD25 variant, or modified to be responsive to an IL-2/13 hybrid, e.g., through expression of IL-13Rα2, may be employed for the treatment of a subject for autoimmune disease.

In one embodiment, cells (e.g., Treg cells) may be collected from a subject having autoimmune disease, modified to have increased sensitivity for IL-2 or to be responsive to an IL-2/13 hybrid and reintroduced into the subject to treat the subject for the autoimmune disease.

In some instances, Treg cells collected from a subject having an autoimmune condition, modified to express a CD25 variant with increased affinity, and reintroduced into the subject may result in an increased immunosuppressive response as compared to infusion of unmodified Treg cells. In some instances, Treg cells collected from a subject having an autoimmune disease, modified to express IL-13Rα2, and reintroduced into the subject may result in increased activity of an immunosuppressive response and/or increased maintenance/expansion of the Treg cells upon administration of an IL-2/13 hybrid.

In some instances, modification of cells to be administered to a subject as part of an ACT therapy for immunosuppression may be limited to introduction of a CD25 variant or IL-13Rα2, as described herein, and may not include introduction of other expressed therapeutic constructs. In other instances, modification of cells to be administered to a subject as part of an ACT therapy for an autoimmune condition may include introduction of a CD25 variant or IL-13Rα2, as described herein, and introduction of other expressed therapeutic constructs, such as e.g., antigen-specific immunotherapeutics, including CARs, engineered T cell receptors, therapeutic antibodies and the like.

In one embodiment, a subject having an autoimmune disease may be administered an effective amount of a population of immune cells (e.g., T cells, Treg cells, etc.) expressing a CAR (e.g., a chimeric autoantibody receptor (CAAR, such as those described in U.S. Patent Application Pub. No. US20170051035A1) as well as those described in Mekala et al., Blood. 2005, 105(5):2090-2.; Moisini et al., J Immunol. 2008, 180(5):3601-11; Riley et al., Immunity. 2009, 30(5):656-65; Esensten et al., Nat Rev Rheumatol. 2009, 5(10):560-5; Jethwa et al., Clin Immunol. 2014, 150(1):51-63; the disclosures of which are incorporated herein by reference in their entirety) and a CD25 variant having increased affinity for IL-2 relative to wild-type CD25. Individual immune cells of the population may express the CAR, the CD25 variant or both. In one embodiment, a subject having an autoimmune disease may be administered an effective amount of a population of immune cells (e.g., T cells, Treg cells, etc.) expressing a TCR engineered for the treatment of autoimmune disease (e.g., such as those described in Alli et al., J Immunol. 2011, 187(11):5521-31; Sauer et al., Int Rev Immunol. 2015, 34(6):460-85; Plesa et al., Blood. 2012, 119(15):3420-30; the disclosures of which are incorporated herein by reference in their entirety) and a CD25 variant having increased affinity for IL-2 relative to wild-type CD25. Individual immune cells of the population may express the CAR, the CD25 variant or both.

Such immunosuppressive effects resulting from the introduced therapeutic (e.g., CAR or TCR) expressing cells may involve the secretion of cytokines, including IL-2. Exogenous IL-2 may or may not be administered concomitantly, including before, during or after, with the population of immune cells. Accordingly, the administered CD25 variant expressing immune cells may, in some instances, be stimulated upon binding of endogenous and/or exogenous IL-2, effectively treating the subject for the autoimmune disease.

In one embodiment, a subject having an autoimmune disease may be administered an effective amount of a population of immune cells (e.g., Treg cells) expressing a therapeutic and IL-13Rα2. Individual immune cells of the population may express both the therapeutic and the IL-13Rα2. The subject may be administered an IL-2/13 hybrid that binds to the IL-13Rα2 expressed by the transferred immune cells thereby activating the transferred immune cells. In some instances, IL-2/13 hybrid binding to an IL-13Rα2 expressed by the transferred immune cells may provide for selective maintenance and/or expansion of the transferred immune cells within the subject. As such cells effectively treat a subject for autoimmune disease, their maintenance and/or expansion as a result of binding IL-2/13 hybrid may increase the effectiveness of the transferred cells as compared corresponding cells not expressing IL-13Rα2.

Autoimmune conditions, to which the herein described methods may be applied, include but are not limited to e.g., Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal osteomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynaud's phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (now termed Granulomatosis with Polyangiitis (GPA)), and the like.

Useful therapeutics for treating autoimmune diseases, and expressible forms thereof, also include therapeutic antibodies for the treatment of autoimmune disease, including but not limited to e.g., Tocilizumab (Actemra), Rituximab (Rituxan), Ofatumumab (Arzerra), Belimumab (Benlysta), Epratuzumab (Lymphocide), Abatacept (Orencia), Golimumab (Simponi), Certolizumab (Cimzia), Sifalimumab, and the like.

As summarized above, cells may, in some instances, be contacted with IL-2 or an IL2/13 hybrid, as appropriate, in vitro or in vivo depending on the particular context in which the cells are employed. Where the cells are contacted with exogenous IL-2 or an IL-2/13 hybrid in vitro, the cytokine is added to the engineered cells in a dose and for a period of time sufficient to activate signaling from the receptor, which may utilize the native cellular machinery, e.g. accessory proteins, co-receptors, and the like; or may utilize introduced components. Any suitable culture medium may be used. The cells thus activated may be used for any desired purpose, including experimental purposes relating to determination of antigen specificity, cytokine profiling, and the like, and for delivery in vivo.

Where the contacting is performed in vivo, an effective dose of engineered cells is infused to the recipient, optionally in combination with or prior to administration of exogenous IL-2 or IL-2/13 hybrid. Dosage and frequency may vary depending on the agent; mode of administration; nature of the cytokine; and the like. It will be understood by one of skill in the art that such guidelines will be adjusted for the individual circumstances. The dosage may also be varied for localized administration, e.g. intranasal, inhalation, etc., or for systemic administration, e.g. intramuscularly (i.m.), intraperitoneally (i.p.), intravenously (i.v.), and the like. Generally at least about $10^4$ engineered cells/kg, at least about $10^5$ engineered cells/kg; at least about $10^6$ engineered cells/kg, at least about $10^7$ engineered cells/kg, or more are administered to the recipient.

Where the engineered cells are T cells, an enhanced immune response may be manifest as an increase in the cytolytic response of T cells towards the target cells present in the recipient, e.g. towards elimination of tumor cells, infected cells; decrease in symptoms of autoimmune disease; and the like.

In some embodiments, the condition is a chronic infection, i.e. an infection that is not cleared by the host immune system within a period of up to 1 week, 2 weeks, etc. In some cases, chronic infections involve integration of pathogen genetic elements into the host genome, e.g. retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses.

Viral pathogens of interest include without limitation, retroviral and lentiviral pathogens, e.g. HIV-1; HIV-2, HTLV, FIV, Sly, etc. Hepatitis B virus, Hepatitis C virus, etc. Microbes of interest, but not limited to the following, include: *Yersinia* sp., e.g. *Y. pestis, Y. pseudotuberculosis, Y enterocolitica*; Franciscella sp.; *Pasteurella* sp.; *Vibrio* sp., e.g. *V. cholerae, V. pamhemolyticus; Legionella* sp., e.g. *L. pneumophila; Listeria* sp., e.g. *L. monocytogenes; Mycoplasma* sp., e.g. *M. hominis, M. pneumoniae; Mycobacterium* sp., e.g. *M. tuberculosis, M. leprae; Rickettsia* sp., e.g. *R. rickettsii, R. typhi; Chlamydia* sp., e.g. *C. trachomatis, C. pneumoniae, C. psittaci; Helicobacter* sp., e.g. *H. pylori*, etc. Also included are intracellular protozoan pathogens, e.g. *Plasmodium* sp, *Trypanosoma* sp., *Giardia* sp., *Toxoplasma* sp.; *Leishmania* sp., etc.

An infection treated with the methods of the invention generally involves a pathogen with at least a portion of its life-cycle within a host cell, i.e. an intracellular phase. The methods of the invention provide for more effective killing of infected cells by the T effector cells of the host organism, relative to such killing in the absence of treatment, and thus are directed to the intracellular phase of the pathogen life cycle. The methods may further include monitoring the patient for efficacy of treatment. Monitoring may measure clinical indicia of infection, e.g. fever, white blood cell count, etc., and/or direct monitoring for presence of the pathogen.

Combination Therapy.

Treatment of a subject for a condition employing a composition and/or cells of the subject disclosure may, in some instances, be combined with one or more additional active agents. In some instances, useful additional active agents may include but are not limited to active agents for treating an infection, active agents for treating cancer, active agents for treating an autoimmune condition, and the like. Alternatively, in some instances, a treatment method of the subject disclosure may exclude one or more additional, including any, active agents such that the treatment described is, e.g., the sole active composition (including cells) administered to the subject to treat the subject for the condition.

As summarized above, treatment may be combined with other active agents, including antibiotics, cytokines, and antiviral agents. Exemplary classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. Cytokines may also be included, e.g. interferon γ, tumor necrosis factor α, interleukin 12, etc. Antiviral agents, e.g. acyclovir, gancyclovir, etc., may also be used in treatment.

Where treatment is directed to cancer, chemotherapeutic agents that can be administered in combination with the engineered cells include, without limitation, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

Targeted therapeutics that can be administered in combination with the engineered cells may include, without limitation, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade); Janus kinase inhibitors, such as tofacitinib; ALK inhibitors, such as crizotinib; Bcl-2 inhibitors, such as obatoclax, venclexta, and gossypol; FLT3 inhibitors, such as midostaurin (Rydapt), IDH inhibitors, such as AG-221, PARP inhibitors, such as lniparib and Olaparib; PI3K inhibitors, such as perifosine; VEGF Receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; and/or small molecule drug conjugates, such as Vintafolide; serine/threonine kinase inhibitors, such as Temsirolimus (Torisel), Everolimus (Afinitor), Vemurafenib (Zelboraf), Trametinib (Mekinist), and Dabrafenib (Tafinlar).

The engineered cells may be administered in combination with an immunomodulator, such as a cytokine, a lymphokine, a monokine, a stem cell growth factor, a lymphotoxin (LT), a hematopoietic factor, a colony stimulating factor (CSF), an interferon (IFN), a transforming growth factor (TGF), such as TGF-α or TGF-β, insulin-like growth factor (IGF), erythropoietin, thrombopoietin, a tumor necrosis factor (TNF) such as TNF-α or TNF-β, vascular endothelial growth factor, integrin, granulocyte-colony stimulating factor (G-CSF), granulocyte macrophage-colony stimulating factor (GM-CSF), an interferon such as interferon-α, interferon-β, or interferon-γ, S1 factor, an interleukin (IL) such as IL-1, IL-1cc, IL-3, IL-4, IL-5, IL-6, IL-7, IL-8, IL-9, IL-10, IL-11, IL-12, IL-13, IL-14, IL-15, IL-16, IL-17, IL-18 IL-21 or IL-25, LIF, kit-ligand, FLT-3, endostatin, and LT.

Tumor specific monoclonal antibodies that can be administered in combination with the engineered cells may include, without limitation, gemtuzumab ozogamicin (Myelotarg), Rituximab (marketed as MabThera or Rituxan), Trastuzumab (Herceptin), Alemtuzumab, Cetuximab (marketed as Erbitux), Panitumumab, Bevacizumab (marketed as Avastin), and Ipilimumab (Yervoy).

Treatment of cancer can be combined with an immune response modulator. Immune checkpoint proteins are immune inhibitory molecules that act to decrease immune responsiveness toward a target cell, particularly against a tumor cell in the methods of the invention. Endogenous responses to tumors by T cells can be dysregulated by tumor cells activating immune checkpoints (immune inhibitory proteins) and inhibiting co-stimulatory receptors (immune activating proteins). The class of therapeutic agents referred to in the art as "immune checkpoint inhibitors" reverses the inhibition of immune responses through administering antagonists of inhibitory signals. Other immunotherapies administer agonists of immune costimulatory molecules to increase responsiveness.

Cellular Compositions.

Engineered cells can be provided in pharmaceutical compositions suitable for therapeutic use, e.g. for human treatment. Therapeutic formulations comprising such cells can be frozen, or prepared for administration with physiologically acceptable carriers, excipients or stabilizers (Remington's Pharmaceutical Sciences 16th edition, Osol, A. Ed. (1980)), in the form of aqueous solutions. The cells will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The cells can be administered by any suitable means, usually parenteral. Parenteral infusions include intramuscular, intravenous (bolus or slow drip), intraarterial, intraperitoneal, intrathecal or subcutaneous administration.

The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

For administration of a protein, such as IL-2 or an IL-2/13 hybrid, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Typically, compositions are prepared as injectables, either as liquid solutions or suspensions; solid forms suitable for solution in, or suspension in, liquid vehicles prior to injection can also be prepared. Proteins can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Kits

Also provided are kits for use in the methods. The subject kits may include an expression vector encoding the engineered CD25 protein, IL-13Rα2, or IL-2/13 hybrid; or a cell comprising the expression vector. Kits may further comprise an effective dose of IL-2 or an IL-2/13 hybrid. In some embodiments, the components are provided in a dosage form (e.g., a therapeutically effective dosage form), in liquid or solid form in any convenient packaging (e.g., stick pack, dose pack, etc.). Reagents for the selection or in vitro derivation of cells may also be provided, e.g. growth factors, differentiation agents, tissue culture reagents; and the like.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

In some embodiments, the subject compositions, methods and kits are used to enhance a T cell mediated immune response. In some embodiments. the immune response is directed towards a condition where it is desirable to deplete or regulate target cells, e.g., cancer cells, infected cells, immune cells involved in autoimmune disease, etc.

The invention now being fully described, it will be apparent to one of ordinary skill in the art that various changes and modifications can be made without departing from the spirit or scope of the invention.

EXAMPLES

Example 1

Figure 2A:
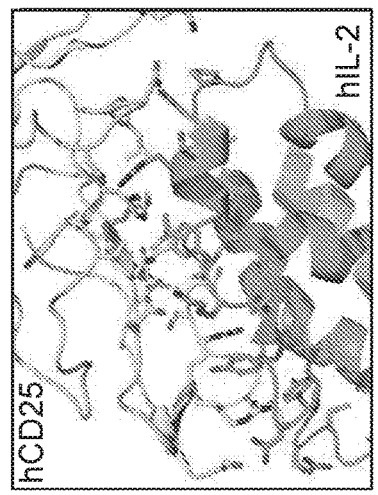
Figure 2B:
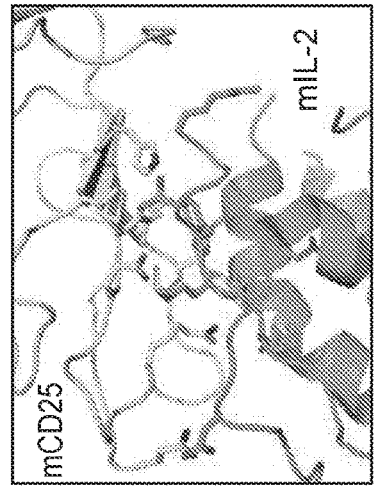

Preparation of CD25 Libraries (FIG. 2).

The complex of WT human CD25 and IL-2 (PDB accession codes 1Z92 and 2B5I) was analyzed by PyMOL and the PDBePISA server. A homology model for WT mouse CD25 and IL-2 was created with Phyre2. Interacting residues were randomized by introducing degenerate codons into the extracellular domain of the CD25 gene. Libraries of mutated CD25 genes were prepared in PCR assembly reactions with oligonucleotides containing the degenerate codons (Eurofins Genomics). EBY100 yeast grown in YPD media were electroporated with the purified CD25 PCR product in addition to pCT vector digested with BamHI/NotI for human CD25, or pYAL vector digested with NheI/HindIII for mouse CD25.

Directed Evolution of Yeast-Displayed CD25 (FIG. 3).

Yeast libraries were cultured in SDCAA media at 30'C, and induced in a mixture of 90% SGCAA and 10% SDCAA media at 20° C. Selections were completed as outlined in FIG. 3. The number of yeast used in each round was at least 10-fold higher than the expected diversity of the remaining library. Yeast cells were washed with PBE and maintained at 4° C. during selections. Cells were incubated with recombinant BH3-tagged hIL-2 or mIL-2 secreted by *Trichoplusia ni* (Hi5) insect cells. Biotinylated IL-2 was purified by FPLC after labeling with BirA enzyme. Yeast were incubated with IL-2 monomer, IL-2 tetramers bound by streptavidin-647, or IL-2 coated streptavidin beads (Miltenyi), except where noted. When applicable, cells were washed and incubated with streptavidin-647 and/or anti-myc antibody, then incubated with anti-647 beads (Miltenyi) for MACS selections or sorted by FACS (Sony SH800). For clone screens, yeast were incubated with IL-2, stained, and analyzed by flow cytometry (Beckman Coulter CytoFLEX).

Surface plasmon resonance (FIG. 4). Sequences of high-affinity CD25 identified from the clone screens were determined by yeast miniprep (Zymo Research), and cloned into pAcBN vectors for expression in Hi5 cells. Soluble high-affinity CD25 proteins were purified by FPLC. Affinity was measured by surface plasmon resonance (Biacore T100), with biotinylated mouse or human IL-2 immobilized on a SA sensor chip (GE Healthcare). CD25 variants were flowed over the chip and the chip was regenerated between runs.

In vitro proliferation assay (FIGS. 5-6). Cell culture plates were coated with 2.5 μg/mL anti-CD3 (BioLegend 145-2C11) in PBS overnight at 4'C. The next day, mouse spleens were harvested and homogenized by pushing them through a 50 μm cell strainer. Cells were washed with mouse T cell media, centrifuged for 4 min. at 1200 rpm, and lysed with ACK buffer at room temperature. Lysis was quenched with media. Cells were then centrifuged and resuspended in media, and placed through a 70 μm strainer. The anti-CD3 coated cell culture wells were washed with PBS, and an equal volume of T cell media with 2×mIL-2/CD28 (BioXCell 37.51) and cell resuspension were added to the wells (final concentration 100 IU/mL mIL-2, 5 μg/mL CD28, $1.5^6$ cells/mL). Cells were activated for 24 hours at 37° C., then were transduced with retrovirus with supplemented with 100 IU/mL mIL-2 and 1:800 polybrene by spinfection at 32° C. and 2500 rpm for 90 min. Retrovirus was collected from 293T cells transfected with a pMSCV-IRES-YFP vector encoding full-length CD25, pCL-Eco packaging vector, and X-tremeGENE reagent in OptiMEM, and sterile-filtered with a 0.45 μm membrane (Millipore). Cells were recovered overnight with mouse T cell media supplemented with 100 IU/mL mIL-2 and harvested. 50,000 cells in 50 μL of T cell media without IL-2 were added to a round-bottom 96 well plate with 50 μL of mouse T cell media with 2× of the IL-2 titration concentration, with 3 wells per concentration. After 48 hours of culture at 37° C., cells were resuspended and an additional 100 μL of mouse T cell media with 1× of the IL-2 titration concentration was added. After 48 hours, cells were resuspended and stained with 50 μL of a 5×DAPI mixture in PBS-FBS, and 30 μL of the resuspension was analyzed by flow cytometry. Data were analyzed by FlowJo and plotted with GraphPad Prism.

Example 2

Figure 8:
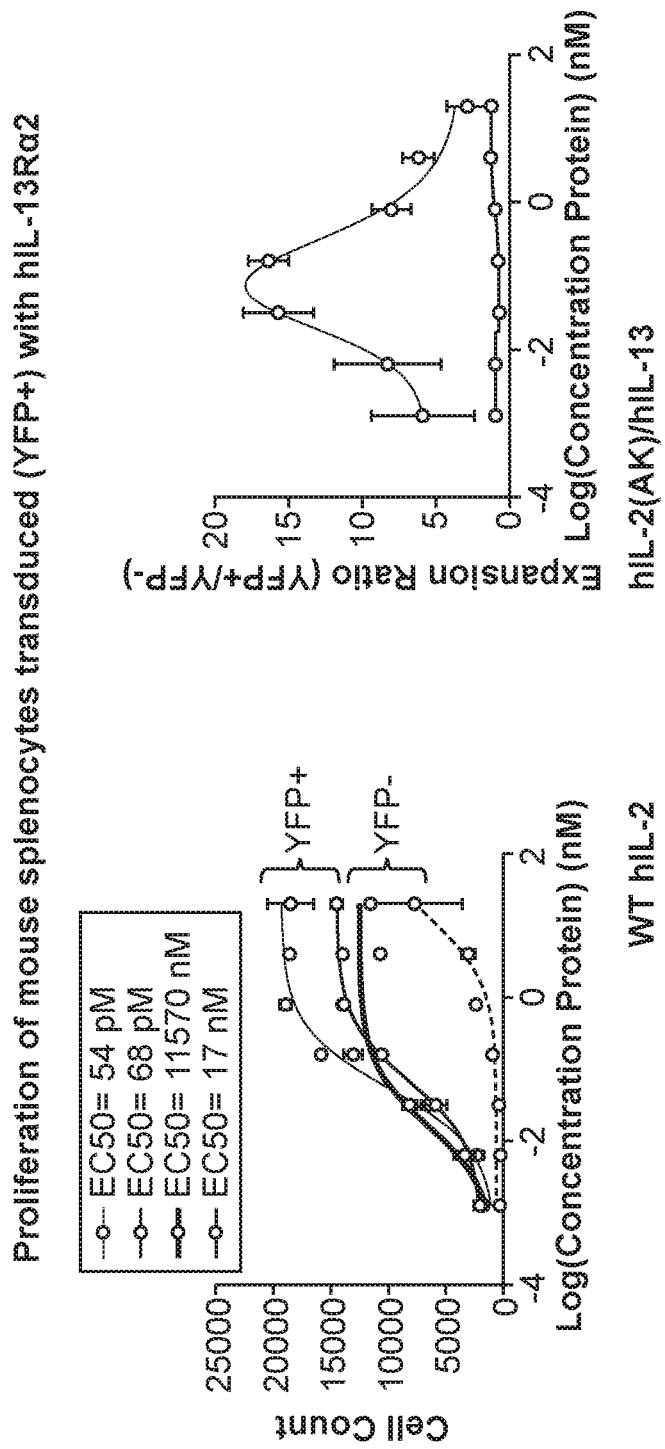

FIG. 8 depicts the results of stimulating cells transfected with IL-13Rα2 with IL-2, or with an IL-2/13 fusion protein. The data indicate that cells engineered with the surrogate hIL-13Rα2 receptor are selectively expanded with the hIL-2(AK)-hIL-13 fusion protein. The experiments were performed as described in Example 1, using IL-13Rα2 as a receptor instead of CD25.

What is claimed is:

1. A modified human CD25 polypeptide engineered to have increased affinity for IL-2, relative to native CD25 protein and affinity of the modified CD25 protein for its cognate IL-2 protein is less than 0.5 nM, comprising a set of amino acid modifications selected from the group consisting of:

(1) D4E, M25A, N27V, E29D, S39Δ, G40Δ, S41T, L42A, I118T, H120L, and K153E;

(2) M25I, N27V, E29D, L42A, I118R, H120W, and K153Q;

(3) L2Q, M25I, N27Y, L42A, I118R, H120W, and K153G;

(4) L2Q, M25V, N27Y, L42A, I118R, and H120W; and (5) M25L, N27V, L42A, I118N, H120M, and K153G.

* * * * *

SEQUENCE LISTING

```
<160> NUMBER OF SEQ ID NOS: 8

<210> SEQ ID NO 1
<211> LENGTH: 251
<212> TYPE: PRT
<213> ORGANISM: H. sapiens

<400> SEQUENCE: 1

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln Val Ala Val Ala Gly
    210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250

<210> SEQ ID NO 2
<211> LENGTH: 247
<212> TYPE: PRT
<213> ORGANISM: M. musculus

<400> SEQUENCE: 2

Glu Leu Cys Leu Tyr Asp Pro Pro Glu Val Pro Asn Ala Thr Phe Lys
```

```
1               5                   10                  15
Ala Leu Ser Tyr Lys Asn Gly Thr Ile Leu Asn Cys Glu Cys Lys Arg
                20                  25                  30
Gly Phe Arg Arg Leu Lys Glu Leu Val Tyr Met Arg Cys Leu Gly Asn
                35                  40                  45
Ser Trp Ser Ser Asn Cys Gln Cys Thr Ser Asn Ser His Asp Lys Ser
                50                  55                  60
Arg Lys Gln Val Thr Ala Gln Leu Glu His Gln Lys Glu Gln Gln Thr
65                  70                  75                  80
Thr Thr Asp Met Gln Lys Pro Thr Gln Ser Met His Gln Glu Asn Leu
                85                  90                  95
Thr Gly His Cys Arg Glu Pro Pro Trp Lys His Glu Asp Ser Lys
                100                 105                 110
Arg Ile Tyr His Phe Val Glu Gly Gln Ser Val His Tyr Glu Cys Ile
                115                 120                 125
Pro Gly Tyr Lys Ala Leu Gln Arg Gly Pro Ala Ile Ser Ile Cys Lys
130                 135                 140
Met Lys Cys Gly Lys Thr Gly Trp Thr Gln Pro Gln Leu Thr Cys Val
145                 150                 155                 160
Asp Glu Arg Glu His His Arg Phe Leu Ala Ser Glu Glu Ser Gln Gly
                165                 170                 175
Ser Arg Asn Ser Ser Pro Glu Ser Glu Thr Ser Cys Pro Ile Thr Thr
                180                 185                 190
Thr Asp Phe Pro Gln Pro Thr Glu Thr Thr Ala Met Thr Glu Thr Phe
                195                 200                 205
Val Leu Thr Met Glu Tyr Lys Val Ala Val Ala Ser Cys Leu Phe Leu
                210                 215                 220
Leu Ile Ser Ile Leu Leu Leu Ser Gly Leu Thr Trp Gln His Arg Trp
225                 230                 235                 240
Arg Lys Ser Arg Arg Thr Ile
                245

<210> SEQ ID NO 3
<211> LENGTH: 133
<212> TYPE: PRT
<213> ORGANISM: H. sapiens

<400> SEQUENCE: 3

Ala Pro Thr Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
                35                  40                  45
Lys Ala Thr Glu Leu Lys His Leu Gln Cys Leu Glu Glu Glu Leu Lys
                50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
                115                 120                 125
```

```
Ile Ser Thr Leu Thr
    130

<210> SEQ ID NO 4
<211> LENGTH: 113
<212> TYPE: PRT
<213> ORGANISM: H. sapiens

<400> SEQUENCE: 4

Pro Gly Pro Val Pro Pro Ser Thr Ala Leu Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Lys Ile Glu Val Ala Gln Phe Val
                85                  90                  95

Lys Asp Leu Leu Leu His Leu Lys Lys Leu Phe Arg Glu Gly Arg Phe
            100                 105                 110

Asn

<210> SEQ ID NO 5
<211> LENGTH: 302
<212> TYPE: PRT
<213> ORGANISM: H. sapiens

<400> SEQUENCE: 5

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Gly Ser Ala Pro Thr Ser Ser Ser Thr Lys
        35                  40                  45

Lys Thr Gln Leu Gln Leu Glu His Leu Leu Leu Asp Leu Gln Met Ile
    50                  55                  60

Leu Asn Gly Ile Asn Asn Tyr Lys Asn Pro Lys Leu Thr Arg Met Leu
65                  70                  75                  80

Thr Phe Lys Phe Tyr Met Pro Lys Lys Ala Thr Glu Leu Lys His Leu
                85                  90                  95

Gln Cys Leu Glu Glu Glu Leu Lys Pro Leu Glu Glu Val Leu Asn Leu
            100                 105                 110

Ala Gln Ser Lys Asn Phe His Leu Arg Pro Arg Asp Leu Ile Ser Asn
        115                 120                 125

Ile Asn Val Ile Val Leu Glu Leu Lys Gly Ser Glu Thr Thr Phe Met
    130                 135                 140

Cys Glu Tyr Ala Asp Glu Thr Ala Thr Ile Val Glu Phe Leu Asn Arg
145                 150                 155                 160

Trp Ile Thr Phe Cys Gln Ser Ile Ile Ser Thr Leu Thr Gly Gly Gly
                165                 170                 175

Gly Ser Pro Gly Pro Val Pro Pro Ser Thr Ala Leu Arg Glu Leu Ile
            180                 185                 190

Glu Glu Leu Val Asn Ile Thr Gln Asn Gln Lys Ala Pro Leu Cys Asn
```

```
            195                 200                 205
Gly Ser Met Val Trp Ser Ile Asn Leu Thr Ala Gly Met Tyr Cys Ala
210                 215                 220
Ala Leu Glu Ser Leu Ile Asn Val Ser Gly Cys Ser Ala Ile Glu Lys
225                 230                 235                 240
Thr Gln Arg Met Leu Ser Gly Phe Cys Pro His Lys Val Ser Ala Gly
                245                 250                 255
Gln Phe Ser Ser Leu His Val Arg Asp Thr Lys Ile Glu Val Ala Gln
                260                 265                 270
Phe Val Lys Asp Leu Leu Leu His Leu Lys Lys Leu Phe Arg Glu Gly
                275                 280                 285
Arg Phe Asn Ala Ala Ala His His His His His His
                290                 295                 300

<210> SEQ ID NO 6
<211> LENGTH: 302
<212> TYPE: PRT
<213> ORGANISM: H. sapiens

<400> SEQUENCE: 6

Met Leu Leu Val Asn Gln Ser His Gln Gly Phe Asn Lys Glu His Thr
1               5                   10                  15
Ser Lys Met Val Ser Ala Ile Val Leu Tyr Val Leu Leu Ala Ala Ala
                20                  25                  30
Ala His Ser Ala Phe Ala Gly Ser Ala Pro Thr Ser Ser Ser Thr Lys
                35                  40                  45
Lys Thr Gln Leu Gln Leu Glu His Leu Leu Leu Asp Leu Gln Met Ile
            50                  55                  60
Leu Asn Gly Ile Asn Asn Tyr Lys Asn Pro Lys Leu Thr Ala Met Leu
65                  70                  75                  80
Thr Lys Lys Phe Tyr Met Pro Lys Lys Ala Thr Glu Leu Lys His Leu
                85                  90                  95
Gln Cys Leu Glu Glu Glu Leu Lys Pro Leu Glu Glu Val Leu Asn Leu
                100                 105                 110
Ala Gln Ser Lys Asn Phe His Leu Arg Pro Arg Asp Leu Ile Ser Asn
                115                 120                 125
Ile Asn Val Ile Val Leu Glu Leu Lys Gly Ser Glu Thr Thr Phe Met
130                 135                 140
Cys Glu Tyr Ala Asp Glu Thr Ala Thr Ile Val Glu Phe Leu Asn Arg
145                 150                 155                 160
Trp Ile Thr Phe Cys Gln Ser Ile Ile Ser Thr Leu Thr Gly Gly Gly
                165                 170                 175
Gly Ser Pro Gly Pro Val Pro Pro Ser Thr Ala Leu Arg Glu Leu Ile
                180                 185                 190
Glu Glu Leu Val Asn Ile Thr Gln Asn Gln Lys Ala Pro Leu Cys Asn
                195                 200                 205
Gly Ser Met Val Trp Ser Ile Asn Leu Thr Ala Gly Met Tyr Cys Ala
            210                 215                 220
Ala Leu Glu Ser Leu Ile Asn Val Ser Gly Cys Ser Ala Ile Glu Lys
225                 230                 235                 240
Thr Gln Arg Met Leu Ser Gly Phe Cys Pro His Lys Val Ser Ala Gly
                245                 250                 255
Gln Phe Ser Ser Leu His Val Arg Asp Thr Lys Ile Glu Val Ala Gln
                260                 265                 270
```

```
Phe Val Lys Asp Leu Leu Leu His Leu Lys Lys Leu Phe Arg Glu Gly
            275                 280                 285

Arg Phe Asn Ala Ala Ala His His His His His His His
        290                 295                 300
```

<210> SEQ ID NO 7
<211> LENGTH: 302
<212> TYPE: PRT
<213> ORGANISM: H. sapiens

<400> SEQUENCE: 7

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Gly Ser Ala Pro Thr Ser Ser Ser Thr Lys
        35                  40                  45

Lys Thr Gln Leu Gln Leu Glu His Leu Leu Leu Asp Leu Gln Met Ile
    50                  55                  60

Leu Asn Gly Ile Asn Asn Tyr Lys Asn Pro Lys Leu Thr Ala Met Leu
65                  70                  75                  80

Thr Lys Lys Phe Tyr Met Pro Lys Lys Ala Thr Glu Leu Lys His Leu
                85                  90                  95

Gln Cys Leu Glu Glu Glu Leu Lys Pro Leu Glu Glu Val Leu Asn Leu
            100                 105                 110

Ala Gln Ser Lys Asn Phe His Leu Arg Pro Arg Asp Leu Ile Ser Asn
        115                 120                 125

Ile Asn Val Ile Val Leu Glu Leu Lys Gly Ser Glu Thr Thr Phe Met
130                 135                 140

Cys Glu Tyr Ala Asp Glu Thr Ala Thr Ile Val Glu Phe Leu Asn Arg
145                 150                 155                 160

Trp Ile Thr Phe Cys Gln Ser Ile Ile Ser Thr Leu Thr Gly Gly Gly
                165                 170                 175

Gly Ser Pro Gly Pro Val Pro Pro Ser Thr Ala Ala Arg Glu Leu Ile
            180                 185                 190

Glu Glu Leu Phe Asn Ile Thr Gln Asn Gln Lys Ala Pro Leu Cys Asn
        195                 200                 205

Gly Ser Met Val Trp Ser Ile Asn Leu Thr Ala Gly Met Tyr Cys Ala
    210                 215                 220

Ala Leu Glu Ser Leu Ile Asn Val Ser Gly Cys Ser Ala Ile Glu Lys
225                 230                 235                 240

Thr Lys Arg Met Leu Ser Gly Phe Cys Pro His Lys Val Ser Ala Gly
                245                 250                 255

Gln Phe Pro Ser Leu His Val Lys Lys Thr Arg Ile Glu Val Ala Gln
            260                 265                 270

Phe Val Lys Asp Leu Leu Ile His Leu Arg Lys Leu Phe Lys Glu Gly
            275                 280                 285

Gln Phe Asn Ala Ala Ala His His His His His His His
        290                 295                 300
```

<210> SEQ ID NO 8
<211> LENGTH: 302
<212> TYPE: PRT
<213> ORGANISM: H. sapiens

<400> SEQUENCE: 8

-continued

```
Met Leu Leu Val Asn Gln Ser His Gln Gly Phe Asn Lys Glu His Thr
1               5                   10                  15
Ser Lys Met Val Ser Ala Ile Val Leu Tyr Val Leu Leu Ala Ala Ala
            20                  25                  30
Ala His Ser Ala Phe Ala Gly Ser Ala Pro Thr Ser Ser Ser Thr Lys
        35                  40                  45
Lys Thr Gln Leu Gln Leu Glu His Leu Leu Leu Asp Leu Gln Met Ile
    50                  55                  60
Leu Asn Gly Ile Asn Asn Tyr Lys Asn Pro Lys Leu Thr Ala Met Leu
65                  70                  75                  80
Thr Lys Lys Phe Tyr Met Pro Lys Lys Ala Thr Glu Leu Lys His Leu
                85                  90                  95
Gln Cys Leu Glu Glu Glu Leu Lys Pro Leu Glu Glu Val Leu Asn Leu
            100                 105                 110
Ala Gln Ser Lys Asn Phe His Leu Arg Pro Arg Asp Leu Ile Ser Arg
        115                 120                 125
Ile Asn Val Ile Val Leu Glu Leu Lys Gly Ser Glu Thr Thr Phe Met
    130                 135                 140
Cys Glu Tyr Ala Asp Glu Thr Ala Thr Ile Val Glu Phe Leu Asn Arg
145                 150                 155                 160
Trp Ile Thr Phe Cys Gln Ser Ile Ile Ser Thr Leu Thr Gly Gly Gly
                165                 170                 175
Gly Ser Pro Gly Pro Val Pro Pro Ser Thr Ala Ala Arg Glu Leu Ile
            180                 185                 190
Glu Glu Leu Phe Asn Ile Thr Gln Asn Gln Lys Ala Pro Leu Cys Asn
        195                 200                 205
Gly Ser Met Val Trp Ser Ile Asn Leu Thr Ala Gly Met Tyr Cys Ala
    210                 215                 220
Ala Leu Glu Ser Leu Ile Asn Val Ser Gly Cys Ser Ala Ile Glu Lys
225                 230                 235                 240
Thr Lys Arg Met Leu Ser Gly Phe Cys Pro His Lys Val Ser Ala Gly
                245                 250                 255
Gln Phe Pro Ser Leu His Val Lys Lys Thr Arg Ile Glu Val Ala Gln
            260                 265                 270
Phe Val Lys Asp Leu Leu Ile His Leu Arg Lys Leu Phe Lys Glu Gly
        275                 280                 285

Gln Phe Asn Ala Ala Ala His His His His His His His His
    290                 295                 300
```